US009765101B2

(12) United States Patent
Hogg et al.

(10) Patent No.: US 9,765,101 B2
(45) Date of Patent: Sep. 19, 2017

(54) ORGANO-ARSENOXIDE COMPOUNDS AND USE THEREOF

(75) Inventors: Philip John Hogg, Malabar (AU); Pierre Dilda, Kingsford (AU)

(73) Assignee: NewSouth Innovations Pty Limited, New South Wales (AU)

( * ) Notice: Subject to any disclaimer, the term of this patent is extended or adjusted under 35 U.S.C. 154(b) by 987 days.

(21) Appl. No.: 13/586,959

(22) Filed: Aug. 16, 2012

(65) Prior Publication Data

US 2013/0041027 A1 Feb. 14, 2013

Related U.S. Application Data

(62) Division of application No. 12/513,159, filed as application No. PCT/AU2007/001676 on Nov. 1, 2007, now Pat. No. 8,268,883.

(30) Foreign Application Priority Data

Nov. 1, 2006 (AU) .................... 2006906220

(51) Int. Cl.
*A61K 31/285* (2006.01)
*C07F 9/76* (2006.01)
(52) U.S. Cl.
CPC ...................... *C07F 9/76* (2013.01)
(58) Field of Classification Search
None
See application file for complete search history.

(56) References Cited

U.S. PATENT DOCUMENTS

| | | | |
|---|---|---|---|
| 2,370,092 A | 2/1945 | Tillitson | |
| 2,409,291 A | 10/1946 | Lott et al. | |
| 2,465,308 A | 3/1949 | Herman et al. | |
| 2,553,515 A | 5/1951 | Herman et al. | |
| 2,664,432 A | 12/1953 | Friedheim | |
| 2,951,766 A | 7/1960 | White | |
| 3,883,650 A | 5/1975 | Friedheim et al. | |
| 5,270,196 A | 12/1993 | Sawada et al. | |
| 5,281,588 A | 1/1994 | Maes et al. | |
| 5,459,263 A | 10/1995 | Floc'H et al. | |
| 7,074,766 B1 | 7/2006 | Hogg et al. | |
| 7,186,695 B2 | 3/2007 | Hogg et al. | |
| 7,498,406 B2 | 3/2009 | Hogg et al. | |
| 7,635,464 B2 | 12/2009 | Hogg et al. | |
| 2001/0044144 A1 | 11/2001 | Anderson et al. | |
| 2005/0101524 A1 | 5/2005 | Hogg et al. | |
| 2006/0166208 A1 | 7/2006 | Hogg et al. | |
| 2007/0037995 A1 | 2/2007 | Hogg et al. | |
| 2007/0037996 A1 | 2/2007 | Hogg et al. | |

FOREIGN PATENT DOCUMENTS

| | | | |
|---|---|---|---|
| FR | 2781674 | 7/1998 | |
| WO | 98/51297 | 11/1998 | |
| WO | 99/18798 | 4/1999 | |
| WO | 99/55344 | 11/1999 | |
| WO | 00/56742 | 9/2000 | |
| WO | 00/79274 | 12/2000 | |
| WO | 01/21628 | 3/2001 | |
| WO | WO 01/21628 | * 3/2001 | ............... C07F 9/20 |
| WO | 02/074305 | 9/2002 | |
| WO | 03/003011 | 1/2003 | |
| WO | 03/039564 | 5/2003 | |
| WO | 2004/042079 | 5/2004 | |
| WO | 2009/043114 | 4/2009 | |

OTHER PUBLICATIONS

Cancer Research UK (accessed online at http://www.cancer-researchuk.org/about-cancer/find-a-clinical-trial/a-trial-looking-at-the-drug-gsao-in-people-with-advanced-cancer#undefined Nov. 7, 2016).*
Beilstein Registry No. 21688.
Beilstein Registry No. 22377.
Beilstein Registry No. 51552.
Beilstein Registry No. 111664.
Beilstein Registry No. 116874.
Beilstein Registry No. 273946.
Beilstein Registry No. 358898.
Beilstein Registry No. 3126376.
Beilstein Registry No. 3129248.
Beilstein Registry No. 3135458.
Beilstein Registry No. 3139905.
Beilstein Registry No. 3141604.
Beilstein Registry No. 3152231.
Beilstein Registry No. 3233826.
Beilstein Registry No. 3235693.
Beilstein Registry No. 3254079.
Beilstein Registry No. 3273842.
Beilstein Registry No. 3275319.
Beilstein Registry No. 3285106.
Beilstein Registry No. 3293148.
Beilstein Registry No. 3296676.
Beilstein Registry No. 3298747.
Beilstein Registry No. 3319010.
Beilstein Registry No. 3341328.
Beilstein Registry No. 3344707.
Beilstein Registry No. 3531489.
Ramachandran, Anup et al., "Apoptosis in the Intestinal Epitheliam: Its Relevance in Normal and Pathophysiological Conditions," Journal of Gastroenterology and Hepatology, 15:109-120 (2000).
Thompson, Craig B., "Apoptosis in the pathogenesis and Treatment of Disease," Science, 267:1456-1462 (1995).
Vermes, Istvan et al., "A Novel Assay for Apoptosis Flow Cytomertic Detectin of Physphatidylserine Expression on Early Apoptoic Cells Using Flueorescein labeled Annexin V," Journal of Immunological Methods, 14:39-51 (1995).

(Continued)

*Primary Examiner* — Craig Ricci
(74) *Attorney, Agent, or Firm* — McDonnell Boehnen Hulbert & Berghoff LLP

(57) ABSTRACT

The present invention relates to organo-arsenoxide compounds and to methods for their synthesis. The invention also relates to pharmaceutical compositions comprising these compounds and to their use in the treatment of diseases and disorders, in particular proliferative diseases and disorders, including treatment of solid tumors and leukaemia.

22 Claims, 17 Drawing Sheets

(56) References Cited

OTHER PUBLICATIONS

Virginio, C. et al., "Kinetics of Cell Lysis, Dye Uptake and Permaeability Chagnes in Cells Expressing the Rat P2x7 Receptor," Journal of PHysiology, 519:335-346 (1999).

Weissleder, Ralph et al., "In Vivo Imaging of Tumors with Protease-Activated Near-INfrared Fluorescent Probes," Nature Biotechnology, 17:375-378 (1999).

Adams, Earle et al., "Chemistry of Organometalloid Complexes with potential Antidotes: Structure of an Organoarsenic(III) Dithiolate Ring," Inorg. Chem., 29:1500-1503 (1990).

Greenberg, N.M. et al., "Prostate Cancer in Transgenic Mouse," PNAS, 92:3429-3443 (1995).

Hofstra, L. et al., "In Vivo Detection of Apoptosis in an Intracardiac Tumor," JAMA, 285(14):1841-1842 (2001).

Kaufmann, Scott H., "Cell Death Induced by Topoisomerase-Targeted Drugs: More Questions Than Answers," Biochimica et Biophysica Acta, 1400:195-211 (1998).

Mattson, Mark P., "Apoptosis in Neurodegenerative Disorders," National Review/Molecular Cell Biology, 1:120-129 (2000).

Novia, Robert, "Protein Disulfide Isomerase: The Multifunctional Redox Chaperone of the Endoplasmic Reticulum," Cell & Developmental Biology, 10:481-493 (1999).

Pronk, Gijsbertus J. et al., "Requirement of an ICE-Like Protease for Induction of Apoptosis and Ceramide Generation by REAPER," Science, 271:808-810 (1996).

Thornberry, Nancy A. et al., "Caspases: Enemies Within," Science, 281:1312-1316 (1998).

Zhu, Huijun et al., "An ICE-Like Protease is a Common Mediator of Apoptosis Induced by Diverse Stimuli in Human Monocytic THP.1 Cells," FEBS Letters, 374:303-308 (1995).

Bazarbachi, Ali et al., Aresenic Trioxide and Interferon-α Synergize to Induce Cell Cycle Arrest and Apoptosis in Human T-Cell Lymphotropic Virus Type I-Transformed Cells, Blood, 93(1):278-283 (1999).

Gitler, Carlos et al., "General Method to Identify and Enrich Vicinal Thiol Proteins Present in Intact Cells in the Oxidized, Disulfide State," Analytical Biochemistry, 252:48-55 (1997).

Parker, Jane et al., The Role of Apoptosis in the Pathogenesis of th Myelodysplastic Syndromes, Int. J. Hematol., 73:416-428 (2001).

O'Reilly, Michael S. et al., "Angiostation: A Novel Angiogenesis Inhibitor That Mediates the Suppression of Metastases by a Lewis Lung Carcinoma," Cell, 79:315-328 (1994).

Nihei, Oscar K. et al., "Pharmacologic Properties of P27/P2X7 Receptor Characterized in Murine Dendritic Cells: Role on the Induction of Apoptosis," Blood, 96(3):996-1004 (2000).

Stone, Martin J. et al., "Recombinant Soluble Human Tissue Factor Secreted by Saccharomyces cerevisiae and Refolded from Escherichia coli Inclusion Bodies: Glycosylation of Mutants, Activity and Physical Characterization," Biochem J., 310:605-614 (1995).

Ju, Shyr-Te et al., "Molecular and Cellular Mech Regulating T and B Cell Apop Through Fax/FasL Interaction," Intern. Rev. Immunol., 18:485-513 (1999).

Jiang, Xing-Mai et al., "Redox Control of Exofacial protein Thiols/Disulfides by protein Disulfide Isomerase," J. Bio. Chem., 4:2416-2423 (1999).

Huang, Xianming et al., "Tumor Infraction in Mice by Antibody-Directed Targeting of Tissue Factor to Tumor Vasculature," Science, 275:547-550 (1997).

Hofstra, Leo et al., "Visualisation of Cell Death in vivo in Patients with Acute Myocardial Infarction," The Lancet, 356:209-212 (2000).

Allen et al., "The mounse Bcrpl/Mxr/Abcp gene: amplification and overexpression in cell lines selected for resistance to topotecan, mitoxantrone, or doxorubicin", Cancer Res., 1999, vol. 59, 4237-4241.

Dilda et al., "Para to ortho repositioning of the arsenical moiety of the angiogenesis inhibitor 4-(N-(S-glutathionylacetyl)amino)phenylarsenoxide results in a markedly increased cellular accumulation and antiproliferative activity", Cancer Res., 2005, vol. 65, 11729-11734.

Dilda et al., "Mechanism of selectivity of an angiogenesis inhibitor from screening a genome-wide set of Saccharomyces cerevisiae deletion strains", J. Natl. Cancer Institute, 2005, vol. 97, 1539-1547.

Don et al., "A peptide trivalent arsenical inhibits tumor angiogenesis by perturbing mitochondrial function in angiogenic endothelial cells", Cancer Cell, 2003, vol. 3, 497-509.

Evens et al., "The potential of arsenic trioxide in the treatment of malignant disease: past, present, and future", Leuk. Res., 2004, vol. 28, 891-900.

Evers et al., Inhibitory effect of the reversal agents V-104, GF120918 and Pluronic L61 on MDR1 Pgp-, MRP1- and MRP2-mediated transport, Br. J. Cancer, 2000, vol. 83, 366-374.

Kobayashi et al., "Involvement of human organic anion transporting polypeptide OATP-B (SLC21A9) in pH-dependent transport across intestinal apical membrane", J. Pharmacol. Exp. Ther., 2003, vol. 306, 703-708.

Kool et al., "MRP3, an organic anion transporter able to transport anti-cancer drugs", Proc. Natl. Acad. Sci., 1999, vol. 96, 6914-6919.

Reiter et al., "Pathogenesis, diagnosis and monitoring of residual disease in acute promyelocytic leukemia", Acta Haematol., 2004, vol. 112, 55-67.

Vey et al., "Arsenic trioxide for the treatment of myelodysplastic syndromes", Expert Opin. Pharmacother., 2004, vol. 5, 613-621.

Wolff et al., "Imatinib mesylate efficiently achieves therapeutic intratumor concentrations in vivo but has limited activity in a xenograft model of small cell lung cancer", Clin. Cancer Res., 2004, vol. 10, 3528-3534.

Sieburg, "Aus dem Institut fur Pharmakologie und physiologische Chemie der Universitat zu Rostock. Ueber Ester aromatischer Arsenverbindungen (der p-Benzarsinsaure) mit Aminosauren und hoheren Alkoholen", Zur Biologie aromatischer Arsenverbindungen, Ztschr. f. physiol. Chem., 1916, 97, Heft 2/3, 224-245.

Hummel et al., "Modification of Bovine Pancreatic Ribonuclease A with the Site-Specific Reagent 4-Arsono-2-nitrofluorobenzene. Spectrophotometric Titration of Arsononitrophenyl Ribonuclease A Derivatives", Biochemistry, 1981, vol. 20, 4843-4852.

Hummel et al., "Chemical modification of ribonuclease A with 4-arsono-2-nitrofluorobenzene", Int. J. Peptide Protein Res., 1984, vol. 24, 1-13.

Delnomdedieu et al., "Reduction and binding of arsenate and dimethylarsinate by glutathione: a magnetic resonance study", Chemico Biological Interactions, 1994, vol. 90, 139-155.

Donoghue, N. et al., "Characterization of Redox-Active Proteins on Cell Surface", Methods in Enzymology, 2002, vol. 348, 76-86.

Hnatowich, DJ et al., "Investigations of Avidin and Biotin for Imaging Applications", 1987, The Journal of Nuclear Medicine, vol. 8, 1294-1302.

Gill, B.S., "Chemotherapeutic Susceptibility of Trypanosoma to some Arsenicals and Suramin-Tryparsamid Complex", Acta Vet., 1971, 40(2), 209-14. (English Abstract only).

Yuki, H. et al., "Synthesis of Purine and Pyrmidine Derivatives of Arsonic Acid", Chem. Pharm. Bull., 1967, 15(7), 1052-1055.

Donahue, N. et al., [9] Identification of Redox-Active Proteins on Cell Surface, Methods of Enzymology, vol. 352, 101-112.

Namgung et al., "Arsenite-Induced Apoptosis in Cortical Neurons Is Mediated by c-Jun N-Terminal Protein Kinase 3 and p38 Mitogen-Activated Protein Kinase," The Journal of Neuroscience, 20(7), 6442-6451 (2000).

Loiseau et al., "Contribution of Dithiol Ligands to In Vitro and In Vivo Trypanocidal Activities of Dithiaarsanes and Investigation of Ligand Exchange in an Aqueous Solution," Antimicrobial Agents and Chemotherapy, 44(11) 2954-2961 (2000).

Gorman et al., "The Hype and the Hope", Time, 1998, 151(19), 40-44. Included HTML pp. 1-9.

Gura, T., "Systems for Identifying New Drugs are Often Faulty", Science, 1997, 278(7), 1041-1042.

Dermer, GB, "Another Anniversary for the War on Cancer", Bio/Technology, 1994, vol. 12, p. 320.

McKie, R., "Cancer Research Set Back a Decade", The Observer, 2001, Jun. 10, 1-4.

(56) References Cited

OTHER PUBLICATIONS

Definition of Cancer. Internet document <<http://www.medterms.com>> 1 page, accessed Sep. 16, 2005, last reviewed Sep. 18, 2004.
Chemical Abstracts Registry No. 1112-90-3. p-amino phenyl arsenoxide.
Chemical Abstracts Registry No. 637-03-6. Arsenosobenzene.
Rudinger, In: Peptide Hormones, JA Parsons, Ed., 1976, 1-7.
Voet et al., Biochemistry, 2nd Edition, 1995, 235-241.
Smilek et al., "A single amino acid change in a myelin basic protein peptide confers the capacity to prevent rather than induce experimental autoimmune encephalomyelitis," Proc. Natl. Acad. Sci., 1991, vol. 88, 9633-9637.
Banks et al., "Biomolecules Bearing the S- or SeAsMe2 Function: Amino Acid and Steroid Derivatives," J. Med. Chem., 1979, 22(5), 572-575.
Cai et al., "Mitochondrial Control of Apoptosis: the role of cytochrome c'Biochimica et Biophysica Acta", 1998, vol. 1366, 139-148.
Korge et al., "Phenylarsine oxide induces mitochondrial permeability transition, hypercontracture, and cardiac cell death," Am. J. Physiol. Heart Circ. Physiol., 280, H2203-H2213 (2001).
Costantini et al., "Modulation of the mitochondrial permeability transition pore by pyridine nucleotides and dithiol oxidation at two separate sites," The journal of Biological Chemistry, 271(12):6746-6751 (1996).
Rimon, Galia et al., "Rapid Communication: Increased Surface Phosphatidylserine Is an Early Marker of Neuronal Apoptosis," Journal of Neuroscience Research, 48:563-570 (1997).
Hortelano et al., "Nitric oxide induces apoptosis via triggering mitochondrial permeability transition," FEBS Letters, 410:373-377 (1997).
Balakirev et al., "Gradual changes in permeability of inner mitochondrial membrane precede the mitochondrial permeability transition," Archives of Biochemistry and Biophysics, 356(1):46-54 (1998).
Costantini et al., "Oxidation of a critical thiol residue of the adenine nucleotide translocator enforces Bcl-2-independent permeability transition core opening and apotpsis," Oncogene, 19:307-314 (2000).
Al-Nasser I.A., "In vivo prevention fo adriamycin carditoxicity by cyclosporin A or FK506," Toxicology, 131:175-181 (1998).
Evtodienko et al., Mechanisms of the Resistances to the Mitochondrial Permeability Transition in Tumor Cells, Pathophysiology, 171-178 (1999).
Riddles, Peter W. et al., "Reassessment of Ellman's Reagent," Methods in Enzymology, 91:5061 (1983).
Ryser, Hugues J.P. et al., Cell Surface Sulfhydryls are Required for the Cytotoxicity of Diphtheria Toxin but not of Ricin in Chinese Hamster Ovary Cells, Journal of Biological Chemistry, 266(28):18439-18442 (1991).
Lawrence, David A. et al., "Surface Thiols of Human Lymphocytes and their Changes after In Vitro and In Vivo Activation," Journal of Leukocyte Biology, 60:611-618 (1996).
Rupnow, B.A. et al., "The Role of Radiation-Induced Apoptosis as a determinant of tumor Responses to radiation Therapy," Apoptosis, 4(2);115-143 (1999).
Stefanec, Tihomir, "Endothelial Apoptosis, Could it Have a Role in the pathogenesis and Treatment of a Disease?" Chest, 117(3):841-854 (2000).
Han, "Advances in Characterization of Pharmaceutical Hydrates," Trends in Bio/Pharmaceutical Industry, pp. 25-29, Mar. 2006.
Vippagunta, et al., Adv Drug Deliv Rev 48:3-26, 2002, WO.
Gottlieb, Roberta A. et al., "Apoptosis in Myocardial Ischemia-Reperfusion," Ann. N.Y. Acad. Sci., 874:412-426 (1999).
Fisher, Karen L. et al., "Cloning and Expression of Human Tissue Factor cDNA," Thrombosis Research, 48:89-99 (1987).
Donoghue, Neil et al., "Presence of Closely Spaced Protein Thiols on the Surface of Mammalian Cells," Protein Science 9:2436-2445 (2000).
Daly, John M. et al., "Neu Differentiation Factor Induces ErbB2 Down-Regulation and Apoptosis of ErbB2-Overexpressing Breast Tumor Cells," Cancer Research, 57:3804-3811 (1997).
Dahmoun, M. et al., "Apoptosis, Proliferation, and Sex Hormone Receptors in Superficial Parts of Human Endometriu at the End of the Secretory Phase," The Journal of Clinical Endocrinology & Metabolism, 84(5):1737-1743 (1999).
Blankenberg, F.G. et al., "Will Imaging of Apoptosis Play a Role in Clinical Care?" A Tale of Mice and Men, Apoptosis, 6:117-123 (2001).
Andre, Harry A.M. et al., "Binding of Vascular Anticoagulant α (VACα) to Planar Phospholipid Bilayers," J. Bio. Chem., 265(9):4923-4926 (1990).
Ades, Edwin W. et al., "HMEC-1: Establishment of an Immortalized Human Microvascular Endothelial Cell Line," The Journal of Investigative Dermatology, 99(6):683-690 (1992).
Anyonymous, "Arthritis: The Aging Populations of Developed Countries are Likely to present a Growing market for Arthritis Therapies," Nature Biotechnology, 18:IT12-IT14 (2000).
Hayes, Andrew J., "Angioneogenesis in Rheumatoid Arthritis," The Lancet, 354:423-424 (1999).
Koch, Alisa Erika, "The Role of Angiogenesis in Rheumatoid Arthritis: Recent Developments," Ann. Rheum. Dis., 59:65-71 (2000).
McStay, Gavin P. et al., "Role of Critical Thiol Groups on the Matrix Surface of the Adenine Nucleotide Translocase in the Mechanism of the Mitochondrial Permeability Transition Pore," Biochem. J., 367:541-548 (2002).
Belzacq, Anne-Sophie et al., The adenine Nucleotide Translocator in Apoptosis, Biochimie, vol. 84, 167-176 (2002).
Fantin, Valeria R. et al., "A Novel Mitochrondriotoxic Small Molecule that Selectively Inhibits Tumor Cell Growth," Cancer Cell, 2:29-42 (2002).
Desagher et al, "Mitochondria as the Central Point of Apoptosis," Trends in Cell Biology, 10:369-377 (2000).
Halestrap, Andrew P. et al., "The Permeability Transition Pore Complex: Another View," Biochimie, 84:153-166 (2002).
Happersberger, Peter H. et al., "A Mass Spectrometric Approach to the Characterization of Protein Folding Reactions," Eur. Mass Spectrom, 4:209-214 (1998).
Rosen, Anders et al., "A CD4+ T Cell Line-Secreted Factor, Growth, Promoting for Normal and Leukemic B Cells, Identified as Thioredoxin," International Immunology, 7(4):625-633 (1995).
Holmgren, Arne, Thioredoxin and Glutaredoxin Systems, J. Bio. Chem., 264(24):13963-13966 (1989).
Bannai et al., "The Export of Glutathione from Human Diploid Cells in Culture," J. Bio. Chem., 254(9):3444-3450 (1979).
Stathakis, Paul et al., "Angiostatin Formation Involves Disulfide Bond Reduction and Proteolysis in Kringle 5 of Plasmin," J. Bio. Chem., 274(13):8910-8916 (1999).
Stathakis, Paul et al., "Generation of Angiostatin by Reduction and Proteolysis of Plasmin: Catalysis by a Plasmin Reductase Secreted by Cultured Cells," J. Bio. Chem., 272(33):20641-2045 (1997).
Tager, Michael et al., "Membrane-Bound Proteindisulfide Isomerase (PDI) is Involved in Regulation of Serface Expression fo Thiols and Drug Sensitivity B-CLL Cells," Experimental Hematology, 25:601-607 (1997).
Essex, David W. et al., "Protein Disulphide Isomerase Mediates Platelet Aggregation and Secretion," British Journal of Haematology, 104:448-454 (1999).
Essex, David W. et al., "Locatization of Protein Disulfide Isomerase to the External Surface of the Platelet Plasma Membrane," Blood, 86(6):2168-2173 (1995).
Zai, Adrian et al., "Cell-Surface Protein Disulfide Isomerase Catalyzes Transnitrosation and Regulates Intracellular Transfer of Nitric Oxide," The Journal of Clinical Investigation, 103(3):393-399 (1999).
Rao, Krishna A.S.M. et al., "cDNA for R-cognin: Homology with a multifunctional protein," PNAS, 90:2950-2954 (1993).
Couet, Jacques et al., "Cell Surface Protein Disulfide-Isomerase is Involved in the Shedding of Human Thyrotropin Receptor Ectodomain," Biochemistry, 35:14800-14805 (1996).

(56) References Cited

OTHER PUBLICATIONS

Mandel, Richard et al., "Inhibition of a Reductive Function of the Plasma Membrane by Bacitracin and Antibodies Against Protein Disulfide-Isomerase," PNAS, 90:4112-4116 (1993).
Pisciotto, Patricia T. et al., "Induction of Mucosal Glutathione Synthesis by Arsenic," Biochemical et Biophysica Acta, 628:241-243 (1980).
Carter, Nicola S. et al., "Arsenical-Resistant Trypanosomes Lack an Unusual Adenosine Transporter," Nature, 361:173-176 (1993).
Bhargava, Kuldeep K. et al., "Effect of Arsenical Drugs on Glutathione Metabolism of Litomosoides Carinii," Molecular and Biochemical Parasitology, 9:29-35 (1983).
Cunningham, Mark L. et al., "Mechanism of inhibition of Trypanothione Reductase and Glutathione Reductase by Trivalent ORganic ARsenicals," FEBS, 221:285-295 (1994).
Fairlamb, Alan H. et al., "Metabolism and Functions of Trypanothione in the Kinetoplastida," Annu. Rev. Microbiol., 46:695-729 (1992).
Fairlamb, Alan H. et al., "Trypanothione is the Primary Target for Arsenical Drugs AGainst African Trypanosomes," PNAS, 86:2607-2611 (1989).
Krams, Sheri et al., "Apoptosis as a Mechanism of Tissue Injury in Liver Allograft Rejection," Seminars in Liver Disease, 18(2):153-167 (1998).
Supplementary European Search Report for EP07815480.

\* cited by examiner

ORGANO-ARSENOXIDE COMPOUNDS AND USE THEREOF

This application is division of U.S. application Ser. No. 12/513,159, filed Sep. 29, 2009, which is a U.S. national phase of International Application No. PCT/AU2007/001676 filed on Nov. 1, 2007, the disclosures of which are hereby incorporated by reference in their entirety.

TECHNICAL FIELD

The present invention relates to organo-arsenoxide compounds and to methods for their synthesis. The invention also relates to pharmaceutical compositions comprising these compounds and to their use in the treatment of diseases and disorders, including proliferative diseases and disorders.

BACKGROUND OF THE INVENTION

Arsenical compounds have been used in the past as therapeutic agents for the treatment of disease. However, the inherent toxicities of arsenical compounds and their generally unfavourable therapeutic index have essentially precluded their use as pharmaceutical agents.

Organo-arsenoxide compounds have been disclosed in WO 01/21628. Such compounds are described as having antiproliferative properties useful in the therapy of proliferative diseases. WO 04/042079 discloses the use of organo-arsenoxide compounds for inducing the mitochondrial permeability transmission (MPT) and the use of organo-arsenoxide compounds for inducing apoptosis, particularly in endothelial cells. The organo-arsenoxide compounds described in WO 01/21628 and WO 04/042079 have a substantially cell-membrane impermeable pendant group linked via a linking group to an arsenoxide group. Neither WO 01/21628 nor WO 04/042079 specifically disclose compounds of formula (I) according to the present invention.

Patients with acute promyelocytic leukaemia (APL) can suffer relapse following treatment with the current therapy, all-trans retinoic acid. In such cases, arsenic trioxide is considered the treatment of choice (Reiter et al., 2004). Arsenic trioxide is a trivalent arsenical that selectively kills APL cells. Arsenic trioxide is also showing promise for the treatment of myelodysplastic syndrome (Vey, 2004), a disease for which no standard treatment currently exists.

However, inorganic arsenicals, such as arsenic trioxide, have long been recognised as a poison and carcinogen when present in the body at levels that exceed its capacity to detoxify the metalloid and are associated with many adverse side effects.

There is a need for alternative therapies for treating proliferative diseases, such as cancer (including treatment of solid tumors), and related conditions. In particular, there is a need for alternative therapies for treating APL, including acute myelocytic leukaemia (AML). There is also a need for a therapeutic treatment for myelodysplastic syndrome.

The present invention relates to a group of arsenoxide compounds comprising an optionally substituted amino acid residue linked via a linking group to a phenylarsenoxide group. Compounds according to the present invention may have one or more advantage(s) over known arsenical compounds, such as arsenic trioxide and the arsenoxide compounds disclosed in WO 01/21628 or WO 04/042079, including the compound 4-(N—(S-glutathionylacetyl) amino)phenylarsenoxide (GSAO), particularly when used for the treatment of proliferative disease, such as cancer (e.g., solid tumors).

SUMMARY OF THE INVENTION

In a first aspect the present invention relates to a compound of general formula (I):

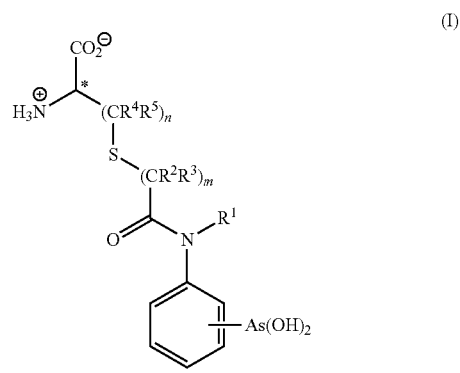

wherein
the $As(OH)_2$ group may be ortho-, meta- or para- to the N-atom on the phenyl ring;
$R^1$ is selected from hydrogen and $C_{1-3}$ alkyl;
$R^2$ and $R^3$ may be the same or different and are independently selected from hydrogen, optionally substituted $C_{1-3}$ alkyl, optionally substituted cyclopropyl, optionally substituted $C_{2-3}$ alkenyl; and optionally substituted $C_{1-3}$ alkoxy;
$R^4$ and $R^5$ may be the same or different and are independently selected from hydrogen, optionally substituted $C_{1-3}$ alkyl, optionally substituted cyclopropyl, optionally substituted $C_{2-3}$ alkenyl; and optionally substituted $C_{1-3}$ alkoxy;
m is an integer selected from 1, 2 and 3;
n is an integer selected from 1, 2 and 3;
* indicates a chiral carbon atom; and
salts and hydrates thereof.

In a second aspect the present invention relates to a pharmaceutical composition comprising at least one compound of formula (I) according to the first aspect of the invention, together with a pharmaceutically acceptable excipient, diluent or adjuvant.

In another aspect the present invention relates to a method of treating a proliferative disease in a vertebrate, the method comprising administering to the vertebrate a therapeutically effective amount of a compound of formula (I) according to the first aspect of the invention, or a composition according to the second aspect of the invention. The proliferative disease may be cancer, such as a solid tumour.

In a further aspect the present invention relates to a method of inhibiting angiogenesis in a vertebrate, comprising administering to the vertebrate an effective amount of a compound of formula (I) according to the first aspect of the invention, or a composition according to the second aspect of the invention.

In another aspect the present invention relates to a method of inducing the Mitochondrial Permeability Transition (MPT) in a vertebrate comprising administering to the vertebrate a therapeutically effective amount a compound of formula (I) according to the first aspect of the invention, or a composition according to the second aspect of the invention.

In a further aspect the present invention relates to a method of inducing apoptosis in proliferating mammalian cells, comprising administering to the mammal an apoptosis-inducing amount of a compound of formula (I) according to the first aspect of the invention, or a composition according to the second aspect of the invention.

In another aspect the invention relates to a method of treating leukaemia or myelodysplastic syndrome in a vertebrate, comprising administering to the vertebrate a therapeutically effective amount of a compound of formula (I) according to the first aspect of the invention, or a composition according to the second aspect of the invention.

In a further aspect the present invention relates to the use of at least one compound of formula (I) according to the first aspect of the invention in the manufacture of a medicament for treating a proliferative disease in a vertebrate. The proliferative disease may be cancer, such as a solid tumour.

In another aspect the present invention relates to the use of at least one compound of formula (I) according to the first aspect of the invention in the manufacture of a medicament for inhibiting angiogenesis in a vertebrate.

In yet another aspect the present invention relates to the use of at least one compound of formula (I) according to the first aspect of the invention in the manufacture of a medicament for inducing the MPT in a vertebrate.

In a further aspect the present invention relates to the use of at least one compound of formula (I) according to the first aspect of the invention in the manufacture of a medicament for inducing apoptosis in proliferating mammalian cells.

In another aspect the present invention relates to the use of at least one compound of formula (I) according to the first aspect of the invention in the manufacture of a medicament for treating leukaemia in a vertebrate.

DEFINITIONS

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In the context of this specification, BRAO refers to 4-(2-bromoacetylamino)benzenearsonic acid; CAO refers to 4-(N—(S-cysteinylacetyl)amino)-phenylarsinous acid; GSAO refers to 4-(N—(S-glutathionylacetyl)amino)phenylarsinous acid; and PENAO refers to 4-(N—(S-penicillaminylacetyl)amino)phenylarsinous acid ["(S)-Penicillamine-arsenoxide"].

As used herein, the term "$C_{1-3}$ alkyl group" includes within its meaning monovalent ("alkyl") and divalent ("alkylene") straight chain or branched chain saturated aliphatic groups having from 1 to 3 carbon atoms. Thus, for example, the term $C_{1-3}$ alkyl includes methyl, ethyl, 1-propyl, and isopropyl.

The term "$C_{2-3}$ alkenyl group" includes within its meaning monovalent ("alkenyl") and divalent ("alkenylene") straight or branched chain unsaturated aliphatic hydrocarbon groups having from 2 to 3 carbon atoms and at least one double bond anywhere in the chain. Unless indicated otherwise, the stereochemistry about each double bond may be independently cis or trans, or E or Z as appropriate. Examples of alkenyl groups include ethenyl, vinyl, allyl, 1-methylvinyl, 1-propenyl, and 2-propenyl.

The term "$C_{2-3}$ alkynyl group" as used herein includes within its meaning monovalent ("alkynyl") and divalent ("alkynylene") unsaturated aliphatic hydrocarbon groups having from 2 to 3 carbon atoms and having at least one triple bond. Examples of alkynyl groups include but are not limited to ethynyl, 1-propynyl.

The term "alkoxy" as used herein refers to straight chain or branched alkyloxy (i.e, O-alkyl) groups, wherein alkyl is as defined above. Examples of alkoxy groups include methoxy, ethoxy, n-propoxy, and isopropoxy.

The term "amino" as used herein refers to groups of the form —$NR^aR^b$ wherein $R^a$ and $R^b$ are individually selected from hydrogen, optionally substituted ($C_{1-4}$)alkyl, optionally substituted ($C_{2-4}$)alkenyl, optionally substituted ($C_{2-4}$)alkynyl, optionally substituted ($C_{6-10}$)aryl and optionally substituted aralkyl groups, such as benzyl. The amino group may be a primary, secondary or tertiary amino group.

In the context of this specification the term "arsenoxide" is synonymous with "arsinous acid" and refers to the moiety $As(OH)_2$, which may also be represented as As=O.

The term "amino acid" as used herein includes naturally and non-naturally occurring amino acids, as well as substituted variants thereof. Thus, (L) and (D) forms of amino acids are included in the scope of the term "amino acid". The term "amino acid" includes within its scope glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine, and histidine. The backbone of the amino acid residue may be substituted with one or more groups independently selected from ($C_{1-6}$)alkyl, halogen, hydroxy, hydroxy($C_{1-6}$)alkyl, aryl, e.g. phenyl, aryl($C_{1-3}$)alkyl, e.g, benzyl, and ($C_{3-6}$)cycloalkyl.

The term "$C_{6-10}$ aryl" or variants such as "arylene" as used herein refers to monovalent ("aryl") and divalent ("arylene") single, polynuclear, conjugated and fused residues of aromatic hydrocarbons having from 6 to 10 carbon atoms. Examples of aromatic groups include phenyl, and naphthyl.

The term "arylalkyl" or variants such as "aralkyl" as used herein, includes within its meaning monovalent ("aryl") and divalent ("arylene"), single, polynuclear, conjugated and fused aromatic hydrocarbon radicals attached to divalent, saturated, straight or branched chain alkylene radicals. Examples of arylalkyl groups include benzyl.

The term "$C_{3-8}$ heterocycloalkyl" as used herein, includes within its meaning monovalent ("heterocycloalkyl") and divalent ("heterocycloalkylene"), saturated, monocyclic, bicyclic, polycyclic or fused hydrocarbon radicals having from 3 to 8 ring atoms, wherein from 1 to 5, or from 1 to 3, ring atoms are heteroatoms independently selected from O, N, NH, or S. The heterocycloalkyl group may be $C_{3-6}$ heterocycloalkyl. The heterocycloalkyl group may be $C_{3-5}$ heterocycloalkyl. Examples of heterocycloalkyl groups include aziridinyl, pyrrolidinyl, piperidinyl, piperazinyl, quinuclidinyl, azetidinyl, morpholinyl, tetrahydrothiophenyl, tetrahydrofuranyl, tetrahydropyranyl, and the like.

The term "$C_{5-20}$ heteroaromatic group" and variants such as "heteroaryl" or "heteroarylene" as used herein, includes within its meaning monovalent ("heteroaryl") and divalent ("heteroarylene"), single, polynuclear, conjugated and fused aromatic radicals having from 5 to 20 atoms, wherein 1 to 6 atoms, or 1 to 4, or 1 to 2 ring atoms are heteroatoms independently selected from O, N, NH and S. The heteroaromatic group may be $C_{5-10}$ heteroaromatic. The heteroaromatic group may be $C_{5-4}$ heteroaromatic. Examples of heteroaromatic groups include pyridyl, pyrimidinyl, pyridazinyl, pyrazinyl, 2,2'-bipyridyl, phenanthrolinyl, quinolinyl, isoquinolinyl, imidazolinyl, thiazolinyl, pyrrolyl, furanyl, thiophenyl, oxazolyl, isoxazolyl, isothiazolyl, triazolyl, and the like.

The term "halogen" or variants such as "halide" or "halo" as used herein refers to fluorine, chlorine, bromine and iodine.

The term "heteroatom" or variants such as "hetero-" as used herein refers to O, N, NH and S.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, haloalkynyl, hydroxyl, hydroxyalkyl, alkoxy, thioalkoxy, alkenyloxy, haloalkoxy, haloalkenyloxy, $NO_2$, $NR^aR^b$, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, aralkyl, alkylheteroaryl, cyano, cyanate, isocyanate, $CO_2H$, $CO_2$alkyl, $C(O)NH_2$, —C(O)NH(alkyl), and —C(O)N(alkyl)$_2$. Preferred substituents include $C_{1-3}$ alkyl, $C_{1-3}$ alkoxy, —CH$_2$—($C_{1-3}$) alkoxy, $C_{6-10}$ aryl, e.g., phenyl, —CH$_2$-phenyl, halo, hydroxyl, hydroxy($C_{1-3}$)alkyl, and halo-($C_{1-3}$)alkyl, e.g., $CF_3$, $CH_2CF_3$. Particularly preferred substituents include $C_{1-3}$ alkyl, $C_{1-3}$ alkoxy, halo, hydroxyl, hydroxy($C_{1-3}$)alkyl, e.g., $CH_2OH$, and halo-($C_{1-3}$)alkyl, e.g., $CF_3$, $CH_2CF_3$.

In the context of this specification the term "administering" and variations of that term including "administer" and "administration", includes contacting, applying, delivering or providing a compound or composition of the invention to an organism, or a surface by any appropriate means.

In the context of this specification, the term "vertebrate" includes humans and individuals of any species of social, economic or research importance including but not limited to members of the genus ovine, bovine, equine, porcine, feline, canine, primates (including human and non-human primates), rodents, murine, caprine, leporine, and avian. In a preferred embodiment the vertebrate is a human.

In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

DETAILED DESCRIPTION OF PREFERRED EMBODIMENTS OF THE INVENTION

Figure 1:
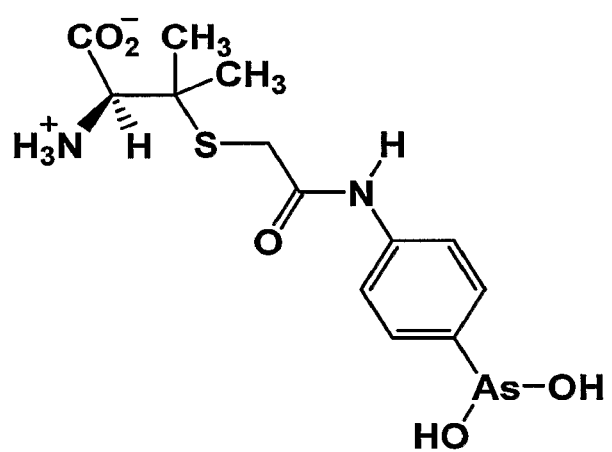
FIG. 1. Structure of (S)-Penicillamine-arsenoxide ("PENAO").

The present invention relates to organo-arsenoxide compounds comprising an optionally substituted amino acid moiety linked via a linker group to a phenylarsenoxide group.

Organo-arsenoxide compounds in accordance with the present invention have a substituted or unsubstituted amino acid moiety. Examples of amino acid moieties include cysteinyl, substituted cysteinyl, for example penicillaminyl (also known as β,β-dimethylcysteinyl or 3-mercaptovalinyl), optionally substituted alaninyl, optionally substituted mercaptoalaninyl, optionally substituted valinyl, optionally substituted 4-mercaptovalinyl, optionally substituted leucinyl, optionally substituted 3- or 4-, or 5-mercaptoleucinyl, optionally substituted isoleucinyl, or optionally substituted 3-, 4- or 5-isoleucinyl. In a preferred embodiment of the invention the amino acid moiety is β,β-dimethylcysteinyl ("penicillaminyl"). In another embodiment of the invention the amino acid moiety is (S)-penicillaminyl. In another embodiment of the invention the amino acid moiety is cysteinyl. The amino acid moiety may have (L), (D), (R) or (S) configuration. Optional substituents include $C_{1-3}$ alkyl, cyclopropyl, $C_{1-3}$ alkoxy, —$CH_2$—($C_{1-3}$)alkoxy, $C_{6-10}$ aryl, —$CH_2$-phenyl, halo, hydroxyl, hydroxy($C_{1-3}$)alkyl, and halo-($C_{1-3}$)alkyl, e.g., $CF_3$, $CH_2CF_3$. In preferred embodiments the optional substituents are independently selected from hydroxyl, methoxy, halo, methyl, ethyl, propyl, cyclopropyl, $CH_2OH$ and $CF_3$.

The linker group of the organoarsenoxide compounds in accordance with the present invention is a substituted or unsubstituted acetamido group. In one embodiment the linker group is an unsubstituted acetamido group.

In particular, the invention relates to compounds of general formula (I):

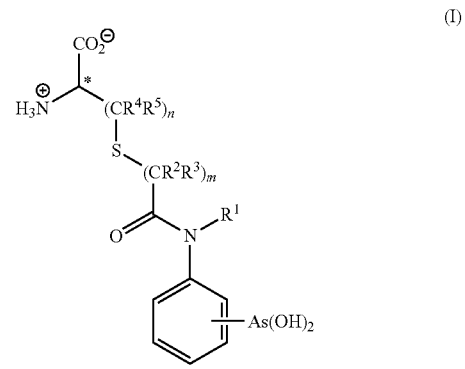

wherein
the As(OH)$_2$ group may be ortho-, meta- or para- to the N-atom on the phenyl ring;
R$^1$ is selected from hydrogen and C$_{1-3}$ alkyl;
R$^2$ and R$^3$ may be the same or different and are independently selected from hydrogen, optionally substituted C$_{1-3}$ alkyl, optionally substituted cyclopropyl, optionally substituted C$_{2-3}$ alkenyl; and optionally substituted C$_{1-3}$ alkoxy;
R$^4$ and R$^5$ may be the same or different and are independently selected from hydrogen, optionally substituted C$_{1-3}$ alkyl, optionally substituted cyclopropyl, optionally substituted C$_{2-3}$ alkenyl; and optionally substituted C$_{1-3}$ alkoxy;
m is an integer selected from 1, 2 and 3;
n is an integer selected from 1, 2 and 3;
* indicates a chiral carbon atom; and
salts and hydrates thereof.

Preferred embodiments of the compounds of general formula (I) are described below. It should be understood that any one or more of the embodiment(s) disclosed herein may be combined with any other embodiment(s), including preferred embodiment(s).

Optional substituents may be the same or different and are independently selected from C$_{1-3}$ alkyl, cyclopropyl, C$_{1-3}$ alkoxy, —CH$_2$—(C$_{1-3}$)alkoxy, C$_{6-10}$ aryl, —CH$_2$-phenyl, halo, hydroxyl, hydroxy(C$_{1-3}$)alkyl, and halo-(C$_{1-3}$)alkyl, e.g, CF$_3$, CH$_2$CF$_3$. In one embodiment the optional substituents are independently selected from hydroxyl, methoxy, halo, methyl, ethyl, propyl, cyclopropyl, CH$_2$OH and CF$_3$. In one embodiment there are no optional substituents.

The As(OH)$_2$ group may be ortho- or para- to the N-atom on the phenyl ring. In one embodiment, the As(OH)$_2$ group is para- to the N-atom on the phenyl ring. In another embodiment the As(OH)$_2$ group is ortho- to the N-atom on the phenyl ring.

R$^1$ may be hydrogen, methyl or ethyl. In one embodiment R$^1$ is hydrogen.

R$^2$ and R$^3$ may be the same or different. R$^2$ and R$^3$ may be independently selected from hydrogen, C$_{1-3}$ alkyl, C$_{2-3}$ alkenyl, C$_{1-3}$ alkoxy, halo(C$_{1-3}$)alkoxy, hydroxy(C$_{1-3}$)alkyl and halo(C$_{1-3}$)alkyl. In a preferred embodiment R$^2$ and R$^3$ may be independently selected from hydrogen, methyl, ethyl, methoxy, vinyl, CH$_2$OH, CF$_3$ and OCF$_3$. In another preferred embodiment R$^2$ and R$^3$ may be independently selected from hydrogen, methyl and ethyl. In another embodiment R$^2$ is methyl and R$^3$ is hydrogen. In another embodiment R$^2$ and R$^3$ are both hydrogen.

R$^4$ and R$^5$ may be the same or different. R$^4$ and R$^5$ may be independently selected from hydrogen, C$_{1-3}$ alkyl, C$_{2-3}$ alkenyl, C$_{1-3}$ alkoxy, halo(C$_{1-3}$)alkoxy, hydroxy(C$_{1-3}$)alkyl and halo-(C$_{1-3}$)alkyl. In a preferred embodiment R$^4$ and R$^5$ may be independently selected from hydrogen, methyl, ethyl, methoxy, vinyl, hydroxy(C$_{1-3}$)alkyl, CF$_3$ and OCF$_3$. In another preferred embodiment R$^4$ and R$^5$ may be independently selected from hydrogen, methyl, ethyl and CH$_2$OH. In another embodiment R$^4$ is methyl or ethyl and R$^5$ is hydrogen or methyl. In another embodiment R$^4$ is methyl and R$^5$ is hydrogen. In another embodiment R$^4$ and R$^5$ are both hydrogen. In another embodiment R$^4$ and R$^5$ are both methyl.

In one embodiment m is 1 or 2. In another embodiment n is 1 or 2. In another embodiment m and n are both 1.

In one embodiment of compounds of formula (I), the As(OH)$_2$ group is ortho- or para- to the N-atom on the phenyl ring; R$^1$ is hydrogen or methyl; R$^2$ and R$^3$ are independently selected from hydrogen, C$_{1-3}$ alkyl, C$_{2-3}$ alkenyl, C$_{1-3}$ alkoxy, halo-(C$_{1-3}$)alkoxy, hydroxy(C$_{1-3}$)alkyl and halo(C$_{1-3}$)alkyl; R$^4$ and R$^5$ are independently selected from hydrogen, C$_{1-3}$ alkyl, C$_{2-3}$ alkenyl, C$_{1-3}$ alkoxy, halo (C$_{1-3}$)alkoxy, hydroxy(C$_{1-3}$)alkyl and halo(C$_{1-3}$)alkyl; m is 1 or 2; and n is 1 or 2.

In another embodiment of compounds of formula (I), the As(OH)$_2$ group is ortho- or para- to the N-atom on the phenyl ring; R$^1$ is hydrogen or methyl; R$^2$ and R$^3$ are independently selected from hydrogen, methyl, ethyl, methoxy, vinyl, CH$_2$OH, CF$_3$ and OCF$_3$; R$^4$ and R$^5$ are independently selected from hydrogen, methyl, ethyl, CH$_2$OH, methoxy, vinyl, CF$_3$ and OCF$_3$; in is 1; and n is 1.

In a further embodiment of compounds of formula (I), the As(OH)$_2$ group is ortho- or para- to the N-atom on the phenyl ring; R$^1$ is hydrogen or methyl; R$^2$ and R$^3$ are independently selected from hydrogen, methyl and ethyl; R$^4$ and R$^5$ are independently selected from hydrogen, methyl and ethyl; m is 1; and n is 1.

In another embodiment of compounds of formula (I), the As(OH)$_2$ group is ortho- or para- to the N-atom on the phenyl ring; R$^1$ is hydrogen or methyl; R$^2$ is hydrogen or methyl; R$^3$ is hydrogen or methyl; R$^4$ is hydrogen, methyl or ethyl; R$^5$ is hydrogen or methyl; m is 1; and n is 1.

In another embodiment of compounds of formula (I), the As(OH)$_2$ group is para- to the N-atom on the phenyl ring; R$^1$ is hydrogen; R$^2$ is hydrogen or methyl; R$^3$ is hydrogen; R$^4$ is hydrogen or methyl; R$^5$ is hydrogen or methyl; m is 1; and n is 1.

In a particular embodiment of the invention the compound of formula (I) is:

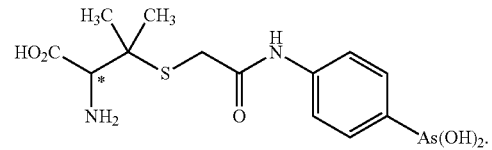

This compound is referred to herein as "Penicillamine-arsenoxide".

In another embodiment of the invention the compound of formula (I) is:

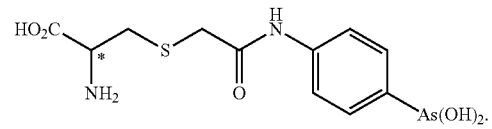

This compound may be referred to herein as "cysteinyl-phenylarsenoxide".

Synthesis of Compounds of Formula (I)

Compounds of formula (I) can be readily prepared by those skilled in the art using methods and materials known in the art and with reference to standard text books, such as "Advanced Organic Chemistry" by Jerry March (third edition, 1985, John Wiley and Sons) or "Comprehensive Organic Transformations" by Richard C. Larock (1989, VCH Publishers).

A representative scheme for the preparation of compounds of formula (I) is shown below:

Scheme 1

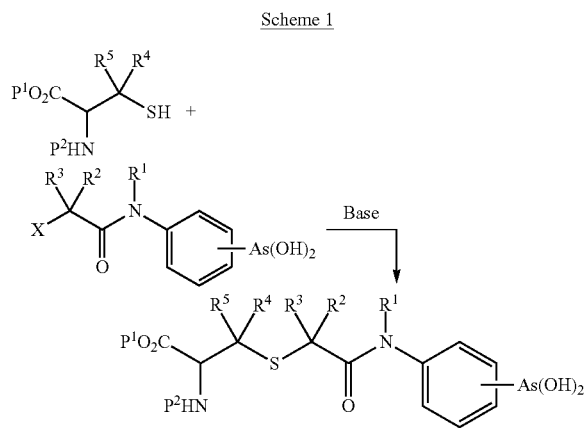

where X is a leaving group and P¹ and P² are hydrogen or protecting groups.

In Scheme 1 X is a leaving group capable of being displaced in a nucleophilic reaction by a nucleophile. Suitable leaving groups include halogens, such as iodo, bromo and chloro. Other suitable leaving groups will be known to those skilled in the art. According to the present invention the nucleophilic group may be a thiol. The —SH may be deprotonated by a base, such as sodium hydroxide, potassium hydroxide, sodium hydrogen carbonate, sodium carbonate, etc. The amino group and/or carboxylic acid group may be protected. Suitable protecting groups are known to those skilled in the art and reference may be had to "Protective Groups in Organic Synthesis" by Theodora Greene and Peter Wuts (third edition, 1999, John Wiley and Sons).

In an alternative synthetic strategy, compounds of formula (I) according to the present invention may be prepared by enzymic cleavage of a peptidyl residue of an organo-arsenoxide compound. Suitable enzyme(s) can be selected depending on the composition of the peptidyl residue. Thus, for example, where an organo-arsenoxide starting compound comprises a tripeptide residue such as glutathione, compounds of formula (I) can be prepared by enzymic cleavage of the terminal γ-glutamyl residue with γ-glutamyl transpeptidase (e.g., ovine kidney γ-glutamyl transpeptidase type I), followed by cleavage of the glycinyl residue with an aminopeptidase (e.g., porcine kidney aminopeptidase) to leave a cysteinyl amino acid residue.

The stereochemistry at the chiral atom indicated by * in formula (I) may be (R) or (S). The present invention includes enantiomerically pure forms of compounds of formula (I), mixtures of enantiomers in any ratio, as well as racemates. In one embodiment of the invention the stereochemistry at the chiral atom indicated by * in formula (I) is (R). In another embodiment the invention the stereochemistry at the chiral atom indicated by * in formula (I) is (S).

In another preferred embodiment of the invention the compound of formula (I) is (S)-Penicillamine-arsenoxide. In another preferred embodiment of the invention the compound of formula (I) is (R)-Penicillamine-arsenoxide. In another embodiment the compound of formula (I) comprises a mixture of (R) and (S) enantiomers of Penicillamine-arsenoxide. In another embodiment, the mixture of (R) and (S) enantiomers of Penicillamine-arsenoxide is a racemic mixture.

In a preferred embodiment of the invention the compound of formula (I) is (S)-cysteinyl-phenylarsenoxide. In another preferred embodiment of the invention the compound of formula (I) is (R)-cysteinyl-phenylarsenoxide. In another embodiment the compound of formula (I) comprises a mixture of (R) and (S) enantiomers of cysteinyl-phenylarsenoxide. In another embodiment, the mixture of (R) and (S) enantiomers of cysteinyl-phenylarsenoxide is a racemic mixture.

Also included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans (E/Z) isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Therapeutic Application(s)

Compounds of formula (I) in accordance with the present invention, and pharmaceutically acceptable salts and hydrates thereof, are capable of binding to cysteine residues of mitochondrial Adenine Nucleotide Translocator (ANT) in proliferating endothelial cells thereby inducing the Mitochondrial Permeability Transition (MPT). Accordingly, compounds of formula (I) according to the present invention may be used to induce proliferation arrest and cell death. Advantageously, compounds of formula (I) may selectively induce the MPT in proliferating endothelial cells, compared to other cells, such as tumor cells. Compounds of formula (I) may therefore be useful in the treatment of proliferative diseases.

Advantageously, compounds of formula (I), such as Penicillamine-arsenoxide and cysteinyl-phenylarsenoxide, may be more effective than known arsenoxide compounds, including organo-arsenoxide compounds disclosed in WO 01/21628, such as the compound 4-(N—(S-glutathionylacetyl)amino)phenylarsenoxide ("GSAO"), at inhibiting cellular proliferation (particularly proliferation of endothelial cells) and/or reducing the viability of endothelial cells. In the context of this invention, "reducing the viability of endothelial cells" can include cell death, or progression towards cell death. For example, compounds of formula (I) may be about 5-times, about 10-times, about 15-times, about 20-times, about 25-times, about 30-times, about 40-times, about 50-times, about 75-times, or about 100-times more effective than GSAO at inhibiting proliferation of endothelial cells and/or reducing the viability of endothelial cells. In a particular embodiment, compounds of formula (I) are from about 5 to 50-times more effective than GSAO at inhibiting proliferation and/or reducing the viability of endothelial cells. In another embodiment, compounds of formula (I) are from about 10 to 30-times more effective than GSAO at inhibiting proliferation and/or reducing the viability of endothelial cells. In another embodiment, compounds of formula (I) are from about 20 to 25-times more effective than GSAO at inhibiting proliferation and/or reducing the viability of endothelial cells.

Advantageously, compounds of formula (I), such as Penicillamine-arsenoxide and cysteinyl-phenylarsenoxide, may be more efficient than known arsenoxide compounds, for example GSAO, at inducing the Mitochondrial Permeability Transition (MPT). For example, the time for half-maximal swelling of isolated mitochondria may be from about 2 to about 20-times, about 2 to about 15-times, about 2 to about 10-times, about 2 to about 8-times, about 2 to about 6-times, or about 2 to about 4-times faster for compounds of formula (I) compared to other arsenoxide compounds, such as GSAO. In a particular embodiment of the invention compounds of formula (I) are from about 2 to about 10-times faster at inducing the MPT than other arsenoxide compounds, such as GSAO. In another embodiment, compounds of formula (I) are from about 2 to about 6-times faster at inducing the MPT than other arsenoxide compounds, such as GSAO. In another embodiment, compounds of formula (I) are from about 4-times faster at inducing the MPT than other arsenoxide compounds, such as GSAO.

The increased efficiency of inhibition of proliferating endothelial cells by compounds of formula (I) according to the present invention may be due to increased accumulation in cells. For example, compounds of formula (I) may accumulate in endothelial cells at a faster rate in comparison to other arsenoxide compounds, such a GSAO. Accordingly, compounds of formula (I) may be more effective inhibitors of cellular proliferation than other organo-arsenoxide compounds, such as GSAO.

Thus, another embodiment of the invention relates to a method of treating a cellular proliferative disease in a vertebrate, the method comprising administering to the vertebrate a therapeutically effective amount of at least one compound of formula (I) or a salt or hydrate thereof, or a pharmaceutical composition thereof. The cells may be endothelial cells. Compounds of formula (I) may be selective for proliferating endothelial cells. Compounds of formula (I) may exhibit greater selectivity for proliferating cells than the compound GSAO. The proliferative disease may be cancer, such as solid tumors. Thus, a particular embodiment of the invention relates to a method of treating solid tumours, the method comprising administering to the vertebrate a therapeutically effective amount of at least one compound of formula (I), or a salt or hydrate thereof, or a pharmaceutical composition thereof. In preferred embodiments, the compound of formula (I) may be Penicillamine-arsenoxide or cysteinyl-phenylarsenoxide.

In another embodiment the present invention relates to a method of inhibiting angiogenesis in a vertebrate, comprising administering to the vertebrate an effective amount of at least one compound of formula (I) or a salt or hydrate thereof, or a pharmaceutical composition thereof.

A further embodiment of the invention relates to a method of selectively inducing the MPT in proliferating cells in a vertebrate comprising administering to the vertebrate a therapeutically effective amount at least one compound of formula (I) or a salt or hydrate thereof, or a pharmaceutical composition thereof. Compounds of formula (I) according to the present invention may induce the MPT by binding to cysteine residues on mitochondrial Adenine Nucleotide Translocator. The compound of formula (I) may be from about 2 to about 20-times, about 2 to about 10-times, about 2 to about 5-times, e.g., about 4-times, more efficient at inducing the MPT in proliferating cells than the compound GSAO.

Another embodiment of the invention relates to a method of inducing apoptosis in proliferating cells in a mammal, comprising administering to the mammal an apoptosis-inducing amount of at least one compound of formula (I) or a salt or hydrate thereof, or a pharmaceutical composition thereof. Compounds of formula (I) may selectively induce apoptosis in proliferating cells relative to normal cells. Compounds of formula (I) may be more effective at inducing apoptosis in proliferating cells than the compound GSAO.

Compounds of formula (I) according to the present invention also have the potential to be useful for treating acute promyelocytic leukaemia (APL). The current treatment of APL is all-trans retinoic acid (ATRA) therapy that targets the underlying molecular lesion and leads to differentiation of leukaemic blasts into mature granulocytes (Reiter et al., 2004). However, treatment with ATRA is associated with the retinoic acid syndrome which can result in death. Relapse is also a problem. In relapsed patients, arsenic trioxide is considered the treatment of choice (Reiter et al., 2004). However, inorganic arsenicals, such as arsenic trioxide, have several disadvantages when used in therapy. For example, inorganic arsenicals, such as arsenic trioxide, have long been recognised as a poison and carcinogen when present in the body, at levels that exceed its capacity to detoxify the metalloid. Arsenic trioxide is administered by intravenous infusion over 2 h to minimize side effects, which include QTc prolongation, APL differentiation syndrome, peripheral neuropathies, hepatic dysfunction and gastrointestinal reactions (Evens et al., 2004). There is a need for safer arsenicals for the treatment of APL, including AML, and myelodysplastic syndrome.

Therefore, a further embodiment of the invention relates to a method of treating leukaemia or myelodysplastic syndrome in a vertebrate, comprising administering to the vertebrate a therapeutically effective amount of at least one compound of formula (I) or a salt or hydrate thereof, or a pharmaceutical composition thereof. In one embodiment the leukaemia is acute promyelocytic leukaemia (APL). In another embodiment the leukaemia is acute myelocytic leukaemia (AML). In accordance with the present invention, compounds of formula (I) may be at least as effective as arsenic trioxide at inhibiting APL cells. In one embodiment, compounds of formula (I) are more effective than arsenic trioxide in treating APL. Advantageously, compounds of formula (I) may exhibit less side effects than arsenic trioxide. Compounds of formula (I) may be more effective than other organoarsenoxide compounds, such as GSAO, in treating APL, AML and/or myelodysplastic syndrome.

Another feature of compounds of formula (I) according to the present invention is that they may have reduced lipid solubility, for example, in comparison to arsenic trioxide. The water solubility of compounds of formula (I) is such that they may have reduced penetration into tissues and be mostly restricted to the intravascular compartment. Therefore, compounds of formula (I) may advantageously may result in less side effects than other arsenicals, such as arsenic trioxide.

Therapeutic advantages may be realised through combination regimens. In combination therapy the respective agents may be administered simultaneously, or sequentially in any order. Accordingly, methods of treatment according to the present invention may involve administration of one or more compounds of formula (I). Compound(s) of formula (I) may be administered in conjunction with conventional therapy, such as radiotherapy, chemotherapy, surgery, or other forms of medical intervention. Examples of chemotherapeutic agents include adriamycin, taxol, fluorouricil, melphalan, cisplatin, oxaliplatin, alpha interferon, vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide, nitrosoureas including carmustine, lomustine, semustine and streptozocin; alkyl sulfonates including busulfan; triazines including dicarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar, and regimens such as COMP (cyclophosphamide, vincristine, methotrexate and prednisone), etoposide, mBACOD (methotrexate, bleomycin, doxorubicin, cyclophosphamide, vincristine and dexamethasone), and PROMACE/MOPP (prednisone, methotrexate (w/leucovin rescue), doxorubicin, cyclophosphamide, taxol, etoposide/mechlorethamine, vincristine, prednisone and procarbazine).

Pharmaceutical and/or Therapeutic Formulations

Typically, for medical use, salts of the compounds of the present invention will be pharmaceutically acceptable salts; although other salts may be used in the preparation of the inventive compounds or of the pharmaceutically acceptable salt thereof. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

Pharmaceutically acceptable salts of compounds of formula I may be prepared by methods known to those skilled in the art, including for example, (i) by reacting a compound of formula I with the desired acid or base; (ii) by removing an acid- or base-labile protecting group from a suitable precursor of the compound of formula I or by ring-opening a suitable cyclic precursor, for example, a lactone or lactam, using the desired acid or base; or (iii) by converting one salt of the compound of formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

Thus, for instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

S. M. Berge et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Convenient modes of administration include injection (subcutaneous, intravenous, etc.), oral administration, inhalation, transdermal application, topical creams or gels or powders, or rectal administration. In one embodiment, the mode of administration is parenteral. In another embodiment, the mode of administration is oral. Depending on the route of administration, the formulation and/or compound may be coated with a material to protect the compound from the action of enzymes, acids and other natural conditions which may inactivate the therapeutic activity of the compound. The compound also may be administered parenterally or intraperitoneally.

Dispersions of compounds according to the invention may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

The compound(s) of the invention may be administered orally, for example, with an inert diluent or an assimilable edible carrier. The compound(s) and other ingredients may also be enclosed in a hard or soft shell gelatin capsule, compressed into tablets, or incorporated directly into an individual's diet. For oral therapeutic administration, the compound(s) may be incorporated with excipients and used in the form of ingestible tablets, buccal tablets, troches, capsules, elixirs, suspensions, syrups, wafers, and the like.

Suitably, such compositions and preparations may contain at least 1% by weight of active compound. The percentage of the compound(s) of formula (I) in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage. "Dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier is an orally administrable carrier.

Another form of a pharmaceutical composition is a dosage form formulated as enterically coated granules, tablets or capsules suitable for oral administration.

Also included in the scope of this invention are delayed release formulations.

Compounds of formula (I) according to the invention also may be administered in the form of a "prodrug". A prodrug is an inactive form of a compound which is transformed in vivo to the active form. Suitable prodrugs include esters, phosphonate esters etc, of the active form of the compound.

In one embodiment, the compound of formula (I) may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the analogue can be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the compounds and/or pharmaceutical compositions according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; for example, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. For example, generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

In another embodiment, a compound of Formula (I) may be administered in an amount in the range from about 100 to about 1000 mg per day, for example, about 200 mg to about 750 mg per day, about 250 to about 500 mg per day, about 250 to about 300 mg per day, or about 270 mg to about 280 mg per day.

Compounds in accordance with the present invention may be administered as part of a therapeutic regimen with other drugs. It may desirable to administer a combination of active compounds, for example, for the purpose of treating a particular disease or condition. Accordingly, it is within the scope of the present invention that two or more pharmaceutical compositions, at least one of which contains a compound of formula (I) according to the present invention, may be combined in the form of a kit suitable for co-administration of the compositions.

The invention will now be described in more detail, by way of illustration only, with respect to the following examples. The examples are intended to serve to illustrate this invention and should not be construed as limiting the generality of the disclosure of the description throughout this specification.

EXAMPLES

Example 1

Preparation and Efficacy of (S)-Penicillamine-Arsenoxide ("PENAO")

Materials and Methods
Synthesis and Purification of (S)-Penicillamine-Arsenoxide:
p-Arsanilic acid (10 g, 46.07 mmol) was dissolved in a 1.18 M Na$_2$CO$_3$ solution, made from Na$_2$CO$_3$ (15 g, 141.5 mmol) dissolved in H$_2$O (120 mL) in a 500 mL round-bottom flask. The solution was cooled in a 4° C. fridge for 2 hours and then placed in an ice bath upon a magnetic stirrer. A solution of bromoacetyl bromide (9 mL, 101.4 mmol) in CH$_2$Cl$_2$ (14 mL) was added in 4 aliquots to the flask while the mixture was vigorously stirred. Addition took about 1 min with CO$_2$ evolution. The mixture was allowed to stir in the ice-bath for 5 min, and then at room temperature for 30 min till CO$_2$ evolution ceased. The mixture was decanted into a 250 mL separatory funnel. Additional CH$_2$Cl$_2$ (10 mL) was added and the layers were allowed to separate for about 10 min. The CH$_2$Cl$_2$ layer was separated and the aqueous layer was placed in a 400 mL beaker. The solution was stirred and acidified with 98% H$_2$SO$_4$ (2.8 mL) to pH 4. A white precipitate resulted which was collected by filtration (14.83 g, 95% yield). The resulting 4-(2-bromoacetylamino)benzenearsonic acid ("BRAO") (14.83 g, 43.88 mmol) was dissolved in 1:1 HBr/MeOH (210 mL) in a 500 mL 3-neck round bottom flask. NaI (5 mg) was added and the mixture was stirred. SO$_2$ was bubbled through at ca. 2 bubbles/second and after 10 min a white precipitate started to form. SO$_2$ was bubbled through for a further 20 h and the mixture was stirred at a medium speed. The solid was collected by filtration, washed with the filtrate then water (30 mL×3), and placed on the rotary evaporator at 50° C. for 5 h to give 4-(2-bromoacetylamino)benzenearsonous acid (6.04 g, 38.8% yield). A portion of the 4-(2-bromoacetylamino)benzenearsonous acid (500 mg, 1.553 mmol) was dissolved in nitrogen-flushed DMSO (10 mL) and added drop-wise over about 1 min to an solution of S-penicillamine (265 mg, 1.77 mmol) in an aqueous NaHCO$_3$ solution (840 mg, 10 mmol) which used nitrogen-saturated H$_2$O (20 mL). The addition took place in a 100 mL round-bottom flask and the clear solution was stirred on a low speed under argon for 4 h. The solution was acidified with 98% H$_2$SO$_4$ (about 0.2 mL) to pH 5. Acetone (500 mL) was stirred vigorously, and the acidified solution was added drop-wise over about 5 min to yield a white precipitate. The supernatant was centrifuged, decanted, and the resulting white solid was further washed and re-centrifuged with acetone (20 mL×2), transferred with acetone (40 mL) into a 100 mL pear-shaped flask and dried on the rotary evaporator at 25° C. for 2 h. Crude Penicillamine-arsenoxide was found to be about 30% pure by internal standard $^1$H-NMR.

Crude (S)-Penicillamine-arsenoxide (100.2 mg, 0.077 mmol as 30% pure) was dissolved in nitrogen-saturated H$_2$O (2.5 mL) and purified on a Low Pressure Liquid Chromatography system. The conditions used were a 30 cm column with a 1.25 cm internal radius, nitrogen-saturated H$_2$O as the running buffer, Biogel P-2 resin and a rate of 0.25 mL/min. The second peak was collected in a 50 mL Falcon tube, frozen in liquid N$_2$, freeze-dried for 3 days, and placed in a desiccator for 1 day to yield dried pure (S)-Penicillamine-arsenoxide (20.3 mg, 0.052 mmol). The process was repeated with more portions of crude Penicillamine-arsenoxide (696 mg in total) and this yielded purified (S)-Penicillamine-arsenoxide (114 mg, 26.5% yield). The structure of (S)-Penicillamine-arsenoxide (FIG. 1) was confirmed by MS, $^1$H-NMR and 2D NMR. The purity obtained was 90% by an arsenical activity assay. The main impurity was water as the final product is extremely hygroscopic. The molecular weight of (S)-Penicillamine-arsenoxide is 390.28 g/mole.

Figure 2:
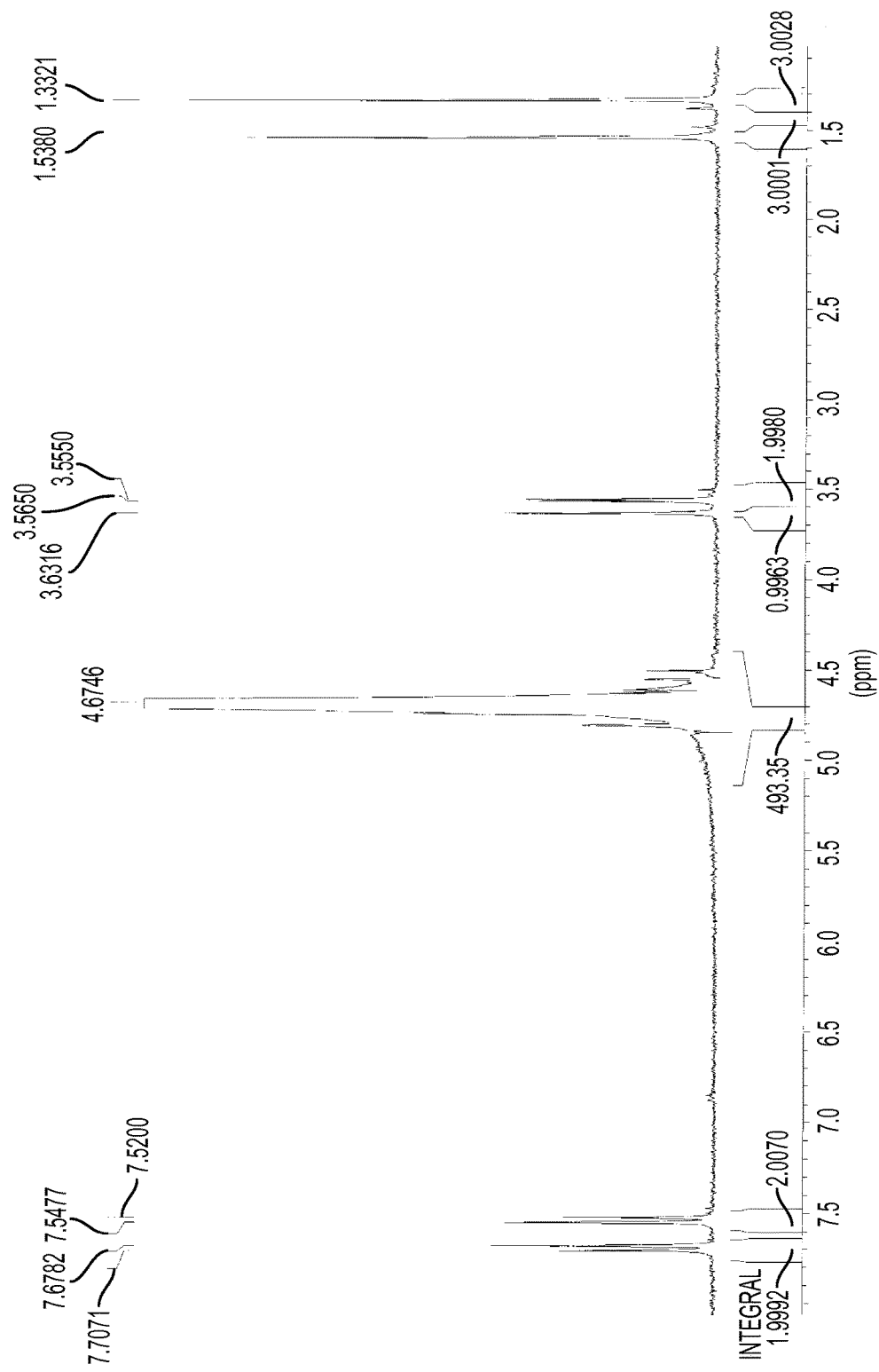
FIG. 2. $^1$H-NMR spectrum of (S)-Penicillamine-arsenoxide.

$^1$H-NMR (300 MHz, D$_2$O): δ 1.32 (s, 3H), 1.53 (s, 3H), 3.55 (d, J=3.4 Hz, 2H), 3.63 (s, 1H), 7.52 (d, J=8.3 Hz, 2H), 7.68 (d, J=8.3 Hz, 2H). The proton NMR spectrum (FIG. 2) was recorded on a Bruker, dual channel probe NMR spectrometer. Rapid keto-enol tautomerism and subsequent deuterium replacement results in the loss of the doublet peak at δ 3.5518 which occurs over 1 h. This can be monitored using time-dependant NMR.

$^{13}$C-NMR (D$_2$O): δ 23.15, 26.83, 33.12, 46.75, 61.36, 121.62, 130.04, 139, 144, 170.

Figure 3:
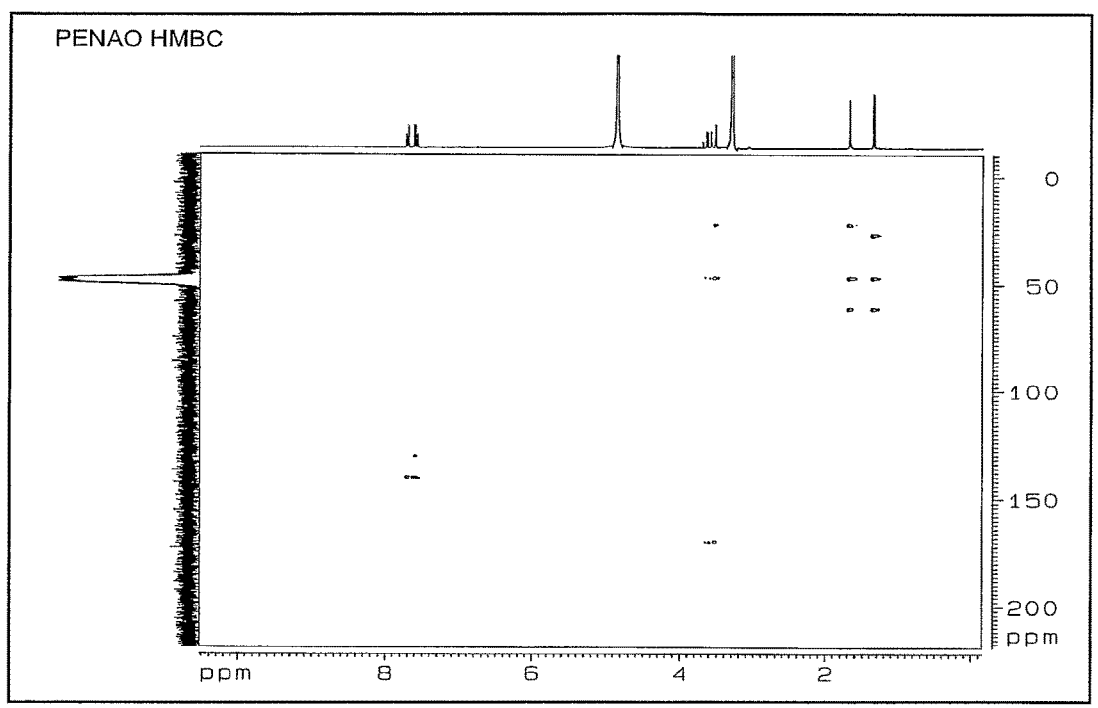
FIG. 3. 2D $^1$H—$^{13}$C multiple bond correlation data for (S)-Penicillamine-arsenoxide. Long-range coupling was observed between the acyl hydrogens of 4-(2-bromoacetylamino)benzenearsonic acid ("BRAO") (δ 3.55) and the penicillamine quaternary carbon (δ 46.75). The NMR spectrum was recorded in $D_2O$ on a 300 MHz Bruker, dual channel probe NMR spectrometer.

The structure of (S)-Penicillamine-arsenoxide was also confirmed by an HMBC experiment (2D $^1$H—$^{13}$C multiple bond coupling, see FIG. 3).

Figure 4:
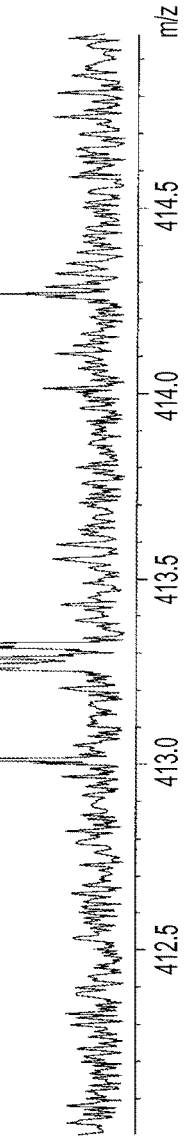
FIG. 4. Mass Spectrometry: sodiated mass peak observed at 413.011678 (δ 1.5 ppm from calculated). Rapid alkyl ester formation occurs depending on the alcohol solvent used e.g, if the sample is run in methanol, the main peaks observed are +15 or +30 mass units.
Figure 4:
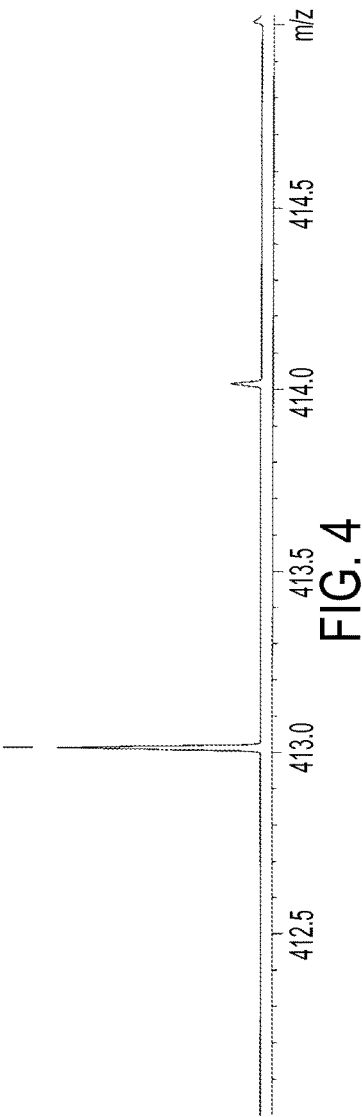

MS: m/z 413.011678 (M+Na)$^+$ (C$_{13}$H$_{19}$SO$_5$N$_2$AsNa requires 413.012285). (FIG. 4)

Synthesis of Penicillamine-arsonic acid
p-Arsanilic acid (10 g, 46.07 mmol) was dissolved in a 1.18 M Na$_2$CO$_3$ solution, made from Na$_2$CO$_3$ (15 g, 141.5 mmol) dissolved in H$_2$O (120 mL) in a 500 mL round-bottom flask. The solution was cooled in a 4° C. fridge for 2 hours and then placed in an ice bath upon a magnetic stirrer. A solution of bromoacetyl bromide (9 mL, 101.4 mmol) in CH$_2$Cl$_2$ (14 mL) was added in 4 aliquots to the flask while the mixture was vigorously stirred. Addition took about 1 min with CO$_2$ evolution. The mixture was allowed to stir in the ice-bath for 5 min, and then at room temperature for 30 min till CO$_2$ evolution ceased. The mixture was decanted into a 250 mL separatory funnel. Additional CH$_2$Cl$_2$ (10 mL) was added and the layers were allowed to separate for about 10 min. The CH$_2$Cl$_2$ layer was separated and the aqueous layer was placed in a 400 mL beaker. The solution was stirred and acidified with 98% H$_2$SO$_4$ (2.8 mL) to pH 4. The resulting white precipitate 4-(2-bromoacetylamino)benzenearsonic acid ("BRAO") was collected by filtration (14.83 g, 95% yield).

A portion of 4-(2-bromoacetylamino)benzenearsonic acid (500 mg, 1.479 mmol) was dissolved in aqueous NaHCO$_3$ solution (420 mg, 4.999 mmol) in H$_2$O (10 mL) and added drop-wise over about 1 min to a solution of (S)-penicillamine (265 mg, 1.77 mmol) in an aqueous NaHCO$_3$ solution (640 mg, 7.618 mmol) in H$_2$O (15 mL). The addition took place in a 100 mL round-bottom flask and the clear solution was stirred on a low speed for 4 h. The solution was acidified with 98% H$_2$SO$_4$ (about 0.25 mL) to pH 5. A 1:1 acetone:ethanol (500 mL) solution was stirred vigorously, and the acidified solution was added drop-wise over about 5 min to yield a white precipitate. The supernatant was centrifuged, which was decanted, and the resulting white solid was further washed and re-centrifuged with 1:1 acetone:ethanol (25 mL×2), transferred with 1:1 acetone:ethanol (50 mL) into a 100 mL pear-shaped flask and dried on the rotary evaporator at 25° C. for 2 h. The resulting (S)-Penicillamine-arsonic acid was found to be about 44% pure by internal standard $^1$H-NMR spectroscopy and was used without further purification (1.022 g, 75% yield). The structure of (S)-Penicillamine-arsonic acid was confirmed by MS, $^1$H-NMR and 2D NMR. The main impurity was water as the final product is extremely hygroscopic. The molecular weight is 406.28 g/mole.

GSAO was prepared as previously described (Don et al., 2003).

A 1 M solution of arsenic trioxide was prepared by dissolving the solid (Sigma, St. Louis, Mo.) in 3 M NaOH prepared in deoxygenated water. The solution was diluted 10-fold in deoxygenated water, the pH adjusted to 7.0 using HCl and stored at 4° C. in an airtight container until use.

Arsenical Assay (S)-Penicillamine-arsenoxide was dissolved in the titration buffer, sterile filtered, and the concentration determined by titrating with dimercaptopropanol and calculating the remaining free thiols with 5,5'-dithiobis(2-nitrobenzoic acid). The solution was stored at 4° C. in the dark until use. There was no significant loss in the active concentration of stock solutions of the arsenicals for at least a month when stored under these conditions.

Mitochondrial Swelling Assay

Mitochondria were isolated from the livers of ~250 g male Wistar rats using differential centrifugation as previously described (Dilda et al., 2005a; Don et al., 2003). The final mitochondrial pellet was resuspended in 3 mM HEPES-KOH, pH 7.0 buffer containing 213 mM mannitol, 71 mM sucrose and 10 mM sodium succinate at a concentration of 30 mg of protein per mL. Mitochondrial permeability transition induction was assessed spectrophotometrically by suspending the liver mitochondria at 0.5 mg of protein per mL at 25° C. in 3 mM HEPES-KOH, pH 7.0 buffer containing 75 mM mannitol, 250 mM sucrose, 10 mM sodium succinate, and 2 μM rotenone. Swelling was measured by monitoring the associated decrease in light scattering at 520 nm using a SpectraMax Plus microplate reader (Molecular Devices, Palo Alto, Calif.).

Cell Culture

BAE cells were from Cell Applications, San Diego, Calif. and BxPC-3, HT1080, LLC, PANC-1, MCF-7, HCT116 and K562 cells were from ATCC, Bethesda, Md. NB4 and MDCK2 cells were from Shane Supple (Kanematsu Laboratories, Royal Prince Alfred Hospital, Sydney, Australia) and P. Borst (The Netherlands Cancer Institute, Amsterdam, The Netherlands). BAE, HT1080, Panc-1, MCF-7, HCT116, MDCK2 and LLC cells were cultured in DMEM. NB4, K562 and BxPC-3 cells were cultured in RPMI medium. The cells were supplemented with 10% foetal calf serum (FBS), 2 mM L-glutamine, and 1 U·mL-1 penicillin/streptomycin. Cell culture plasticware was from Techno Plastic Products (Trasadingen, Switzerland). All other cell culture reagents were from Gibco (Gaithersburg, Md.).

Cell Proliferation and Viability Assays.

BAE, NB4, K562, MDCK2, HT1080, LLC, HCT116, Panc-1, MCF-7 and BxPC-3 cells were seeded at a density of $1.5 \times 10^3$, $3 \times 10^3$, $4 \times 10^3$, $5 \times 10^2$, $2 \times 10^3$, $5 \times 10^2$, $5 \times 10^2$, $6 \times 10^3$, $6 \times 10^3$ and $1 \times 10^4$ cells per well, respectively, into 96-well plates. Adherent cells were allowed to adhere overnight. They were then cultured for 72 h in medium containing 10% fetal calf serum and (S)-Penicillamine-arsenoxide. Viable cells were determined by incubating cells with the tetrazolium salt MTT (Sigma, St. Louis, Mo.), which is metabolized by viable cells to form insoluble purple formazan crystals. DMSO was added to lyse cells, the contents of the wells were homogenized and the absorbance measured at 550 nm. Cell number in the untreated control was normalized as 100%, and viable cell number for all treatments was expressed as percentage of control. The cytotoxic effects of (S)-Penicillamine-arsenoxide were assayed by flow cytometry with propidium iodide. BAE cells were seeded at a density of $5 \times 10^4$ cells per well into 12-well plates, allowed to adhere overnight, then treated for 48 h with GSAO. Adherent cells were detached with trypsin/EDTA and combined with the growth medium containing the cells that had detached during treatment. The combined cells were pelleted, resuspended in 0.5 mL serum-free medium containing 1 μg·mL$^{-1}$ propidium iodide (Molecular Probes, Eugene, Oreg.) and analysed by flow cytometry.

Flux of (S)-Penicillamine-arsenoxide.

BAE cells were seeded at a density of $1.5 \times 10^6$ cells in Petri dishes and allowed to adhere overnight. Cells were incubated with 50 μM (S)-Penicillamine-arsenoxide at discrete times for up to 2 h at 37° C. and then washed three times with ice-cold PBS. The washed cells were lysed in 1 mL of 70% w/w nitric acid. Petri dishes were then washed twice with 1 mL of PBS and kept at 4° C. until use. Samples were diluted 10-fold and analysed for arsenic atoms using an Elan 6100 Inductively Coupled Plasma Spectrometer (Perkin Elmer Sciex Instruments, Shelton, Conn.).

Organic Anion Transporting Polypeptide (OATP) Studies.

750,000 BAE cells were seeded in 6 well plates containing DMEM with 10% fetal calf serum and allowed to adhere overnight. Cells were pretreated or not with 500 μM 4,4'-diisothiocyanostilbene-2,2'-disulfonic acid (DIDS) for 30 min and then incubated with 20 μM (S)-Penicillamine arsenoxide for 2 h at 37° C. and 5% CO$_2$. Cells were then washed twice with ice-cold PBS and lysed with 70% nitric acid. Cellular arsenic levels were determined by ICPMS. 5000 BAE cells were seeded in 96 well plates containing DMEM with 10% fetal calf serum and allowed to adhere overnight. Cells were pretreated or not with 300 μM DIDS for 30 mM and then incubated with 1.5 μM (S)-Penicillamine arsenoxide for 24 h at 37° C. and 5% CO$_2$. Cell viability was determined using MTT.

Drug Transporter Transfectants.

Transfectants of the Madin-Darby canine kidney II (MDCKII) polarised epithelial cell line, over-expressing multidrug resistance-associated proteins (MRP) 1, 2 or 3, have been described (Evers et al., 2000; Kool et al., 1999), as have the MEF/MDR1 clone H4 over-expressing human MDR1 or BCRP (Dilda et al., 2005b). Cells were grown and maintained as adherent monolayers in DMEM containing 10% calf serum (Cosmic™, Hyclone, Tauranga, New Zealand), 100 μg·mL$^{-1}$ penicillin and 60 μg·mL$^{-1}$ streptomycin. Cytotoxicity assays were performed as described previously (Allen et al., 1999).

Primary Tumor Growth Assays.

Female 7 to 9 week old Balb C nude mice were used (UNSW Biological Resource Centre). Mice were held in groups of 3 to 5 at a 12 h day and night cycle and were given animal chow and water ad libidum. A suspension of 2×10$^6$ BxPC-3 cells in 0.2 mL of PBS was injected subcutaneously in the proximal midline. Tumors were allowed to establish and grow to a size of ~50 mm$^3$ after which they were randomized into four groups. Tumor volume was calculated using the relationship length×height×width×0.523. Tumor doubling time ($T_D$) was calculated from the tumor growth rate curve during exponential growth using the formula $T_D$=0.693/ln($V_F/V_I$), where $V_F$ is final tumor volume and $V_I$ is initial tumor volume (Wolff et al., 2004). Animals were implanted with 28 day alzet model 1004 micro-osmotic pumps (ALZA Corporation, Palo Alto, Calif.) subcutaneously in the flank. The pumps delivery 0.25, 0.5 or 1 mg/kg/day (S)-Penicillamine arsenoxide in 100 mM glycine. Tumor volume and animal weight was measured every 2 or 3 days.

Statistical Analyses.

Results are presented as means±SD. All tests of statistical significance were two-sided, and P values<0.05 were considered statistically significant.

Figure 5:
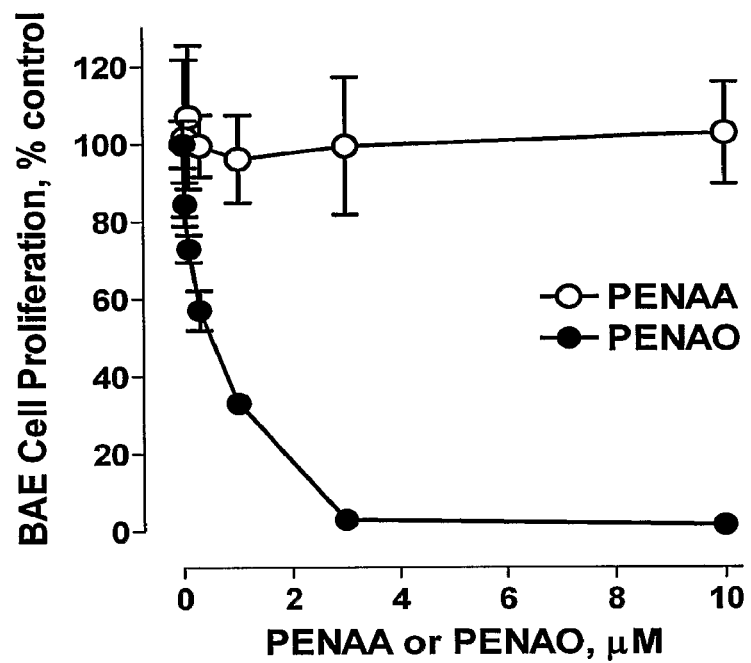
FIG. 5. (S)-Penicillamine-arsenoxide inhibits proliferation of BAE cells with an $IC_{50}$ of 0.4 μM. The pentavalent arsenical compound (S)-Penicillamine-arsenonic acid, has no effect on proliferation. The data points are mean±SD of three experiments performed in triplicate.
Figure 6:
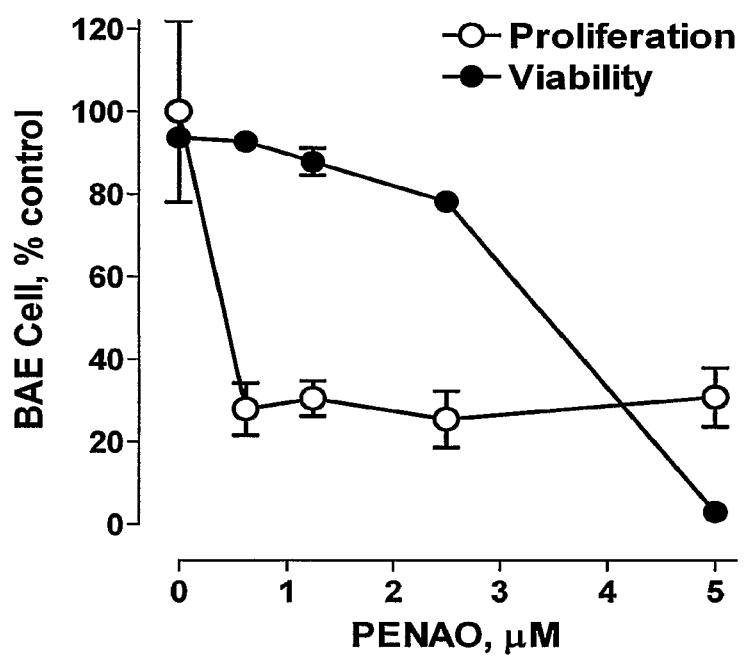
FIG. 6. Comparison of the effects of (S)-Penicillamine-arsenoxide on BAE proliferation versus viability. The data points are mean±SD of three experiments performed in triplicate.

Results and Discussion (S)-Penicillamine-Arsenoxide Inhibits Proliferation of Mammalian Cells Reported IC$_{50}$ values for proliferation arrest and loss of viability of bovine aortic endothelial cells (BAE) cells induced by GSAO are 10 μM and 75 μM, respectively (Dilda et al., 2005a; Don et al., 2003). The IC$_{50}$ for proliferation arrest of BAE cells is 0.4 μM for (S)-Penicillamine-arsenoxide (FIG. 5) compared to 10 μM for GSAO, while the IC$_{50}$ value for loss of viability is 3.5 μM (FIG. 6). (S)-Penicillamine-arsenoxide, therefore, is ~25-times more effective than GSAO at blocking proliferation and reducing the viability of endothelial cells.

Figure 7:
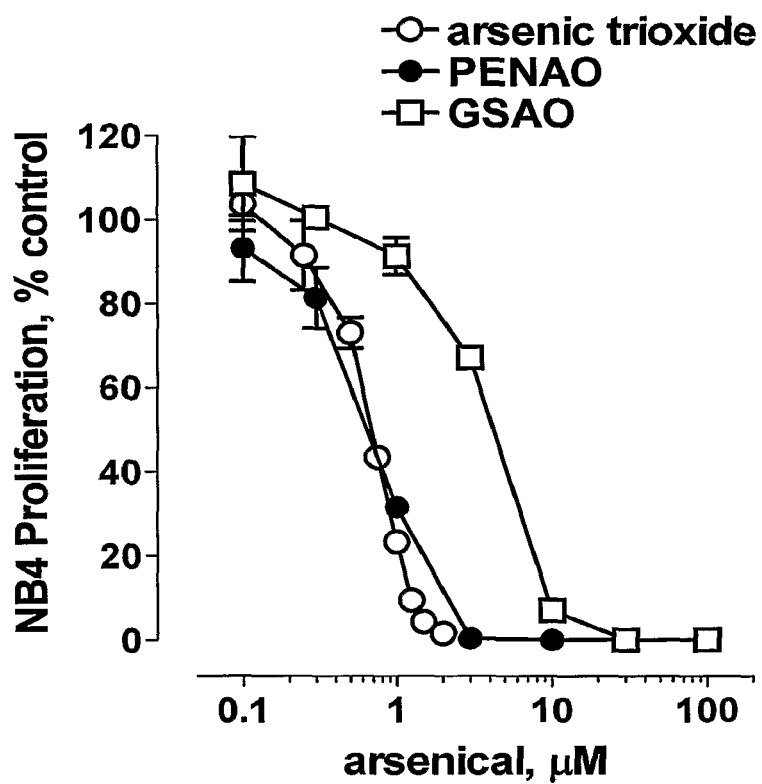
FIG. 7. (S)-Penicillamine-arsenoxide is as good an inhibitor of APL cell proliferation as arsenic trioxide. Number of viable NB4 cells remaining after 72 h incubation with increasing concentrations of arsenic trioxide, Penicillamine-arsenoxide or GSAO. Data points are the mean±SD of triplicate determinations.

(S)-Penicillamine-arsenoxide is a selective inhibitor of endothelial cells compared to tumour cells. Comparison of the IC$_{50}$ for proliferation arrest of endothelial and epithelial cells compared to eight different tumour cell lines is shown in Table 1. All tumour cells tested were 1.6 to 30-fold more resistant to (S)-Penicillamine-arsenoxide than endothelial cells. BAE cells were also 5.6-fold more sensitive to (S)-Penicillamine-arsenoxide than kidney epithelial cells. (S)-Penicillamine-arsenoxide is equivalent to arsenic trioxide in its effects on APL cells, while GSAO is ~10-fold less active (FIG. 7).

TABLE 1

(S)-Penicillamine-arsenoxide IC$_{50}$ values for proliferation arrest for various cell lines.

| Cell Type | Cell Line | IC$_{50}$, μM |
|---|---|---|
| bovine aortic endothelial | BAEC | 0.43 |
| human acute promyelocytic leukaemia | NB4 | 0.70 |
| human chronic myelogenous leukaemia | K562 | 1.4 |
| dog kidney epithelial | MDCK2 | 2.4 |
| human fibrosarcoma | HT1080 | 4.0 |
| human lung carcinoma | LLC | 5.0 |
| human colorectal carcinoma | HCT1116 | 6.0 |
| human pancreatic carcinoma | PANC-1 | 6.5 |

TABLE 1-continued (S)-Penicillamine-arsenoxide IC$_{50}$ values for proliferation arrest for various cell lines.

| Cell Type | Cell Line | IC$_{50}$, μM |
|---|---|---|
| human mammary carcinoma | MCF-7 | 9.0 |
| human pancreatic carcinoma | BxPC-3 | 13 |

Figure 8:
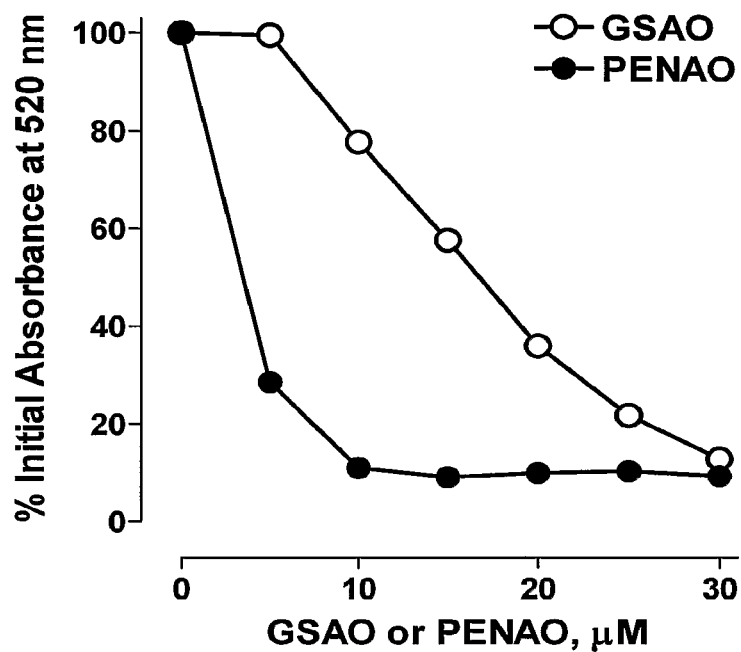
FIG. 8. (S)-Penicillamine-arsenoxide is more efficient than GSAO at inducing the mitochondrial permeability transition. Mitochondrial swelling induced by 100 μM GSAO or (S)-Penicillamine-arsenoxide as measured by decrease in light scattering at 520 nm over 30 min. The traces are representative of two experiments performed in duplicate on two different mitochondrial preparations.

(S)-Penicillamine-arsenoxide is also more efficient than GSAO at inducing the mitochondrial permeability transition. (S)-Penicillamine-arsenoxide, like GSAO, triggered swelling of isolated rat liver mitochondria in a time- and concentration-dependent manner (FIG. 8). The time for half-maximal swelling of isolated mitochondria was approximately 4 times faster for (S)-Penicillamine-arsenoxide compared to GSAO.

Figure 9:
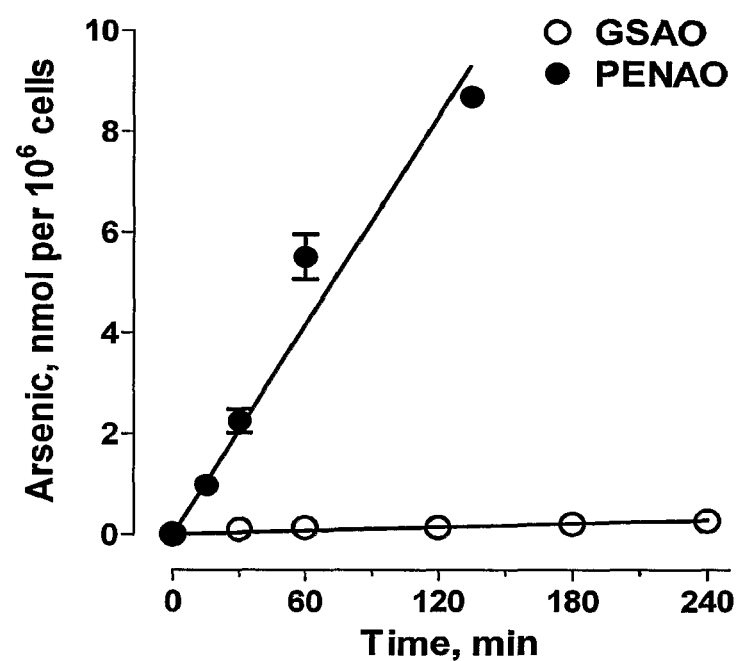
FIG. 9. (S)-Penicillamine-arsenoxide accumulates in BAE cells at a ~70-fold faster rate than GSAO. BAE cells were incubated for up to 4 h in presence of 50 μM GSAO or (S)-Penicillamine-arsenoxide and cytosolic arsenic was measured by inductively coupled plasma spectrometry. The data points and error bars are the mean±SD of triplicate determinations and is representative of two experiments.

Without intending to be bound by any particular theory, a possible mechanism for the increased anti-proliferative activity of (S)-Penicillamine-arsenoxide compared to GSAO was increased accumulation in cells. This theory was tested by comparing the uptake of the two compounds in endothelial cells by measuring cellular accumulation of arsenic. (S)-Penicillamine-arsenoxide accumulated in BAE cells at an approximately 70-fold faster rate than GSAO (FIG. 9). The initial rates of accumulation of GSAO and (S)-Penicillamine-arsenoxide were 1 and 69 pmol per 10$^6$ cells per min, respectively.

OATP is Involved in (S)-Penicillamine Transport Across the Plasma Membrane

Figure 10:
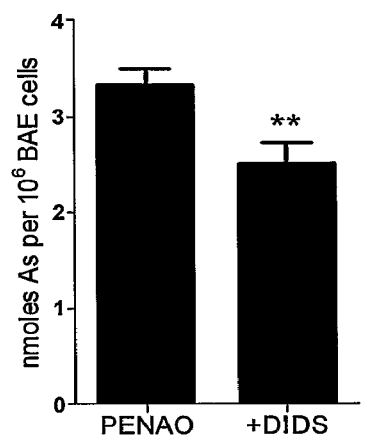
FIG. 10. Inhibition of cell-surface OATP blunts cellular accumulation of (S)-Penicillamine-arsenoxide and anti-proliferative activity. A. Inhibition of (S)-Penicillamine-arsenoxide accumulation in endothelial cells by the OATP inhibitor, DIDS. Cells were pretreated or not with 500 μM DIDS for 30 min and then incubated with 20 μM (S)-Penicillamine-arsenoxide for 2 h. Arsenic content was determined by ICPMS. Values are mean±SD of triplicate determinations. The results are representative of two experiments. : p<0.01. B. DIDS blunts GSAO anti-proliferative activity in endothelial cells. BAE cells were pretreated or not with 300 μM DIDS for 30 mM and then incubated with 1.5 μM (S)-Penicillamine-arsenoxide for 24 h. Cell viability was determined using MTT. Results are expressed as percentage of control. Values are mean±SD of triplicate determinations. Results are representative of two experiments. : p<0.01.
Figure 10:
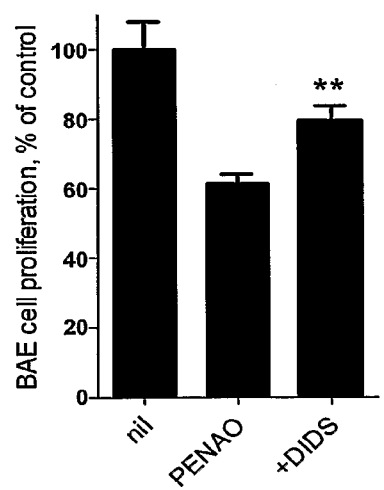

DIDS is an inhibitor of the plasma membrane organic anion transporting polypeptide (OATP) (Kobayashi et al., 2003). The finding that this compound inhibits (S)-Penicillamine arsenoxide uptake (FIG. 10A) and reduces its anti-proliferative activity (FIG. 10B) in BAE cells implies that this transporter is involved in (S)-Penicillamine arsenoxide uptake into these cells.

(S)-Penicillamine Arsenoxide is Exported from the Cell by MRP1 and 2

Figure 11:
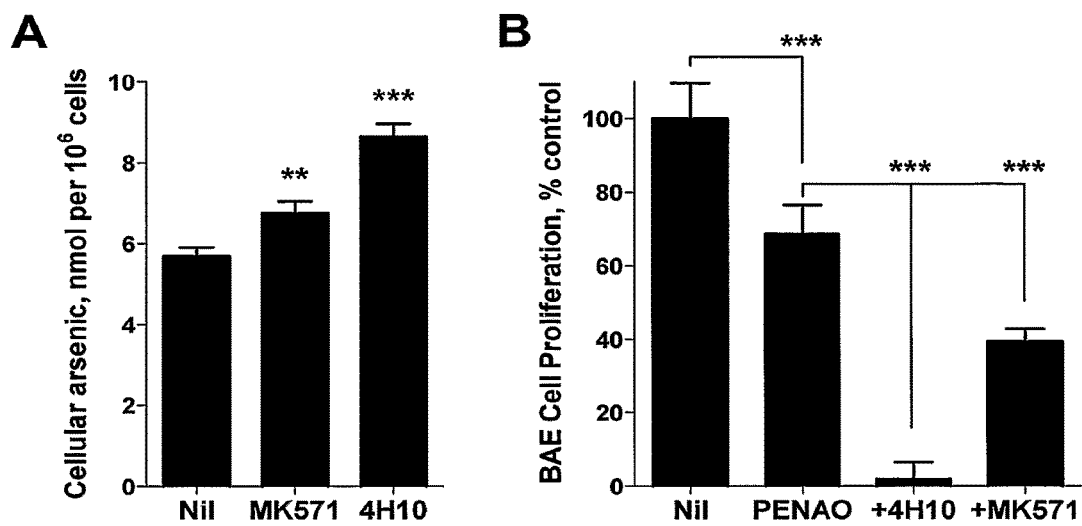
FIG. 11. (S)-Penicillamine-arsenoxide is pumped out of cells by MRP1/2. A BAE cells were incubated for up to 2 h with 50 μM (S)-Penicillamine-arsenoxide in the absence or presence of 4H10 (5 μM) or MK-571 (25 μM) and cytosolic arsenic was measured by inductively coupled plasma spectrometry. The data points and error bars are the mean±SD of quadruplicate determinations and is representative of two experiments. B Effect of the MRP1/2 inhibitors, 4H10 (2 μM) and MK-571 (15 μM), on Penicillamine-arsenoxide (0.3 μM) inhibition of BAE cell proliferation. The MRP inhibitors were incubated for 30 min with the cells prior to incubation with (S)-Penicillamine-arsenoxide for 72 h. The data points and error bars are the mean±SD of triplicate determinations. * is p<0.001,  is p<0.01

MRP1/2 mediates export of GSAO from BAE cells (Dilda et al., 2005b). Penicillamine-arsenoxide is also a substrate for MRP1/2. More (S)-Penicillamine-arsenoxide accumulated in BAE cells in the presence of the MRP1/2 inhibitors 4H10 and MK-571 (FIG. 11A), which correlated with more potent anti-proliferative effect (FIG. 11B). The inhibitors alone had no effect on BAE cell proliferation (data not shown).

Mammalian cells over-expressing MRP1, 2, 3 or 6, or MDR1 or BCRP were tested for resistance to (S)-Penicillamine-arsenoxide. MRP1, MRP2 or MRP3 was over-expressed in the canine kidney epithelial MDCKII cell line, while MRP6, MDR1 or BCRP was over-expressed in the murine embryo fibroblast MEF3.8 line. Cells were exposed to the indicated concentrations of (S)-Penicillamine-arsenoxide for 96 h and the number of viable cells measured and expressed relative to the number of untreated cells. Resistance factor is calculated relative to the (S)-Penicillamine arsenoxide IC$_{50}$ for proliferation arrest of non-transfected parental cells.

TABLE 2

Resistance of mammalian cells over-expressing different drug transporters to (S)-Penicillamine-arsenoxide.

| Transporter | Resistance Factor |
|---|---|
| MD/MRP1 | 3.7 |
| MD/MRP2 | 4.6 |

TABLE 2-continued

Resistance of mammalian cells over-expressing different drug transporters to (S)-Penicillamine-arsenoxide.

| Transporter | Resistance Factor |
|---|---|
| MD/MRP3 | 0.8 |
| MEF/MRP6 | 1.3 |
| MEF/MDR1 | 1.2 |
| MEF/BCRP | 1.1 |

These results indicate that both GSAO and (S)-Penicillamine-arsenoxide are exported from BAE cells by MRP1/2.

Figure 12:
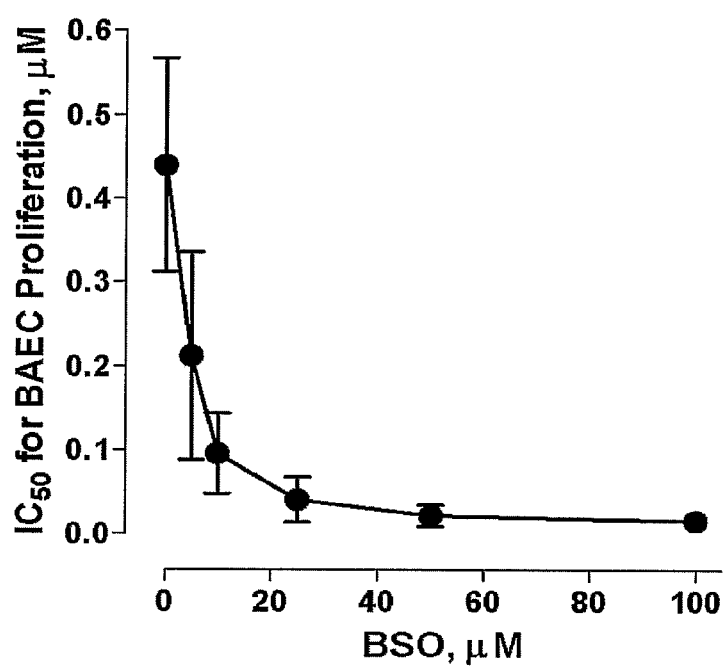
FIG. 12. Depletion of cellular glutathione increases (S)-Penicillamine-arsenoxide anti-proliferative activity. BAE cells were co-treated with (S)-Penicillamine-arsenoxide and the indicated concentrations of BSO for 72 h and the $IC_{50}$ for proliferation arrest was calculated. The data points and error bars are the mean±SD from two experiments performed in triplicate.

Treatment of BAE cells with glutathione reduced GSAO inhibition of BAE cell proliferation, while blocking de novo synthesis of glutathione with buthionine sulfoximine (BSO), an inhibitor of the γ-glutamyl cysteine synthase, enhanced the proliferation arrest by almost 100-fold (Dilda et al., 2005b). These results indicated that MRP1/2 requires cellular glutathione for efficient transport of GSAO from the cell. Similar to the findings with GSAO, treating BAE cells with BSO enhanced the (S)-Penicillamine-arsenoxide $IC_{50}$ for proliferation arrest by approximately 25-fold (FIG. 12).

These results indicate that (S)-Penicillamine-arsenoxide is a more effective inhibitor of endothelial cells because it accumulates in the cells at a much faster rate than GSAO.

Anti-Tumour Activity of (S)-Penicillamine Arsenoxide

Figure 13:
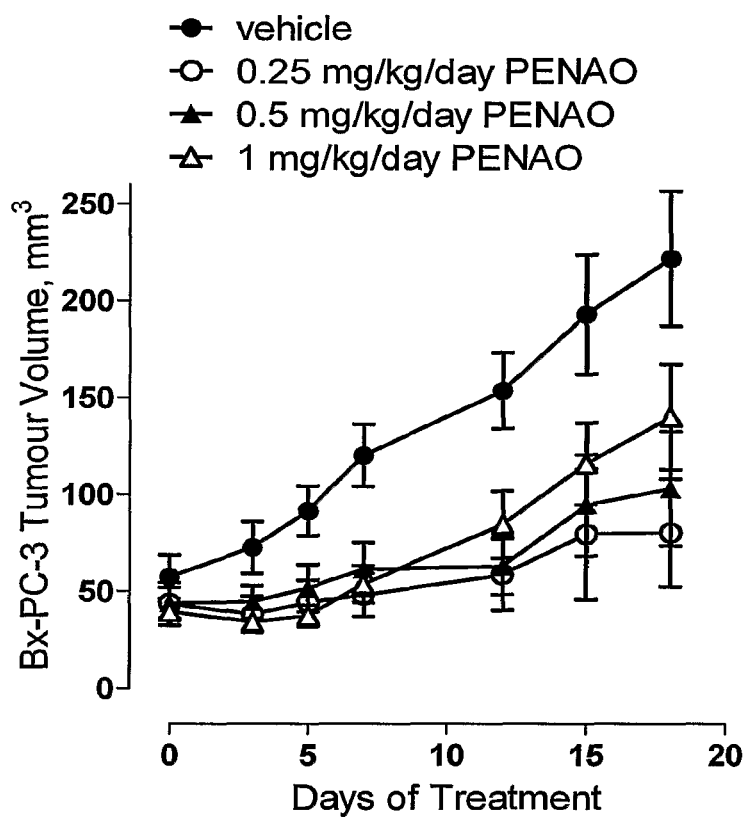
FIG. 13. Inhibition of human pancreatic carcinoma tumour growth by continuous subcutaneous administration of (S)-Penicillamine-arsenoxide. BxPC-3 tumours were established in the proximal midline of female 7 to 9 week old BalbC nude mice. Mice bearing ~50 mm³ tumours were implanted with 28 day alzet micro-osmotic pumps subcutaneously in the flank. The pumps delivered 0.25, 0.5 or 1 mg/kg/day (S)-Penicillamine-arsenoxide in 100 mM glycine (vehicle).

BalbC nude mice bearing subcutaneous human BxPC-3 pancreatic carcinoma tumours in the proximal midline were implanted with 28 day micro-osmotic alzet pumps subcutaneously in the flank. The pumps delivered 0.25, 0.5 or 1 mg per kg per day (S)-Penicillamine arsenoxide. The growth of the BxPC-3 tumours was significantly inhibited in the mice receiving (S)-Penicillamine arsenoxide (FIG. 13). The tumour doubling times are 9.2, 8.3, 13.9 and 16.2 days for groups treated with vehicle (100 mM glycine) or 0.25, 0.5 and 1 mg/kg/day (S)-Penicillamine arsenoxide, respectively.

There was no change in the weight of the vehicle-versus (ω-Penicillamine arsenoxide-treated animals (not shown). There was some skin toxicity at the pump delivery site in the highest dose animals. There was skin necrosis at the delivery site in 3 of the 10 mice and in 1 mouse there was an accumulation of connective tissue. There was some evidence of accumulation of connective tissue at the delivery site in the occasional mouse at the lower doses of (S)-Penicillamine arsenoxide.

Example 2

Preparation and Efficacy of 4-(N—(S-Cysteinylacetyl)amino)-phenylarsinous acid ("CAO")

Materials and Methods
Cell Proliferation Assay

Bovine aortic endothelial (BAE) cells were from Cell Application (San Diego, Calif.). BAE cells were cultured in DMEM supplemented with 10% fetal calf serum, 2 mM L-glutamine, and 5 units per mL penicillin and streptomycin (Gibco, Gaithersburg, Md.). Cells were cultured at 37° C. in a 5% $CO_2$, 95% air atmosphere. BAE cells were seeded in 96-well plates (5,000 cells per well) in 0.2 ml of culture medium. After 24 h of growth, the medium was replaced with fresh culture medium supplemented with GSAO, CAO or 4H10 and cells were cultured for an additional 24, 48 or 72 h. Viable attached cells were determined using the tetrazolium salt MTT (Sigma, St. Louis, Mo.) according to the manufacturer's protocol. Results were expressed as percentage of untreated controls.

Preparation of CAO

Figure 14:
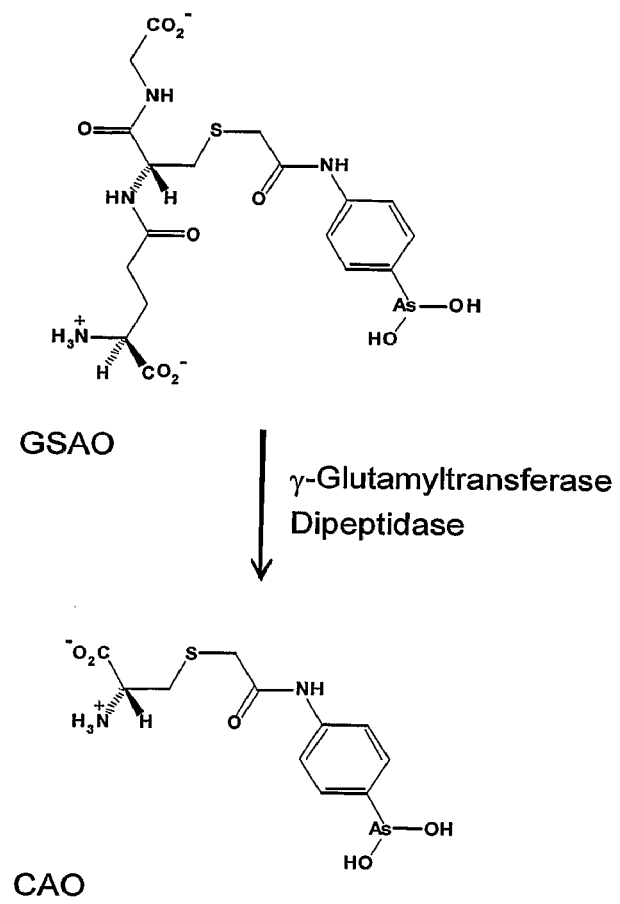
FIG. 14. Production of CAO by enzymatic cleavage of GSAO.

GSAO was produced as described previously (WO 01/21628) to a purity>94% by HPLC. A 50 mM solution of GSAO was made by dissolving solid in 20 mM Hepes, pH 7.0 buffer containing 0.14 M NaCl, 20 mM glycine and 1 mM EDTA. 4-(N—(S-cysteinylglycylacetyl)amino)phenylarsinous acid was produced by cleaving the γ-glutamyl group from GSAO with ovine kidney γ-glutamyl transpeptidase type I (Sigma, product number G8040) (FIG. 14). A 10 mM solution of GSAO was incubated with 0.55 units per ml γGT in 15 mM Tris, pH 7.4 buffer containing 40 mM glycyl-glycine for 1 h at 30° C. The γGT was removed from the reaction by filtration using a YM3 Microcon membrane (Millipore, Billerica, Mass.).

4-(N—(S-cysteinylacetyl)amino)phenylarsinous acid (CAO) was produced by cleaving the glycine amino acid from 4-(N—(S-cysteinylglycylacetyl)amino)phenylarsinous acid with porcine kidney aminopeptidase N (Type IV-S, Sigma, product number L5006) (FIG. 14). The filtrate was incubated with 2 units per ml aminopeptidase N for 1 h at 37° C. The aminopeptidase N was removed from the reaction by filtration using a YM3 Microcon membrane (Millipore). The concentration of CAO was measured by titrating with dimercaptopropanol and calculating the remaining free thiols with 5,5'-dithiobis(2-nitrobenzoic acid) (Don et al., 2003). The titrated solutions were sterile filtered and stored at 4° C. in the dark until use.

HPLC Analysis

Figure 15:
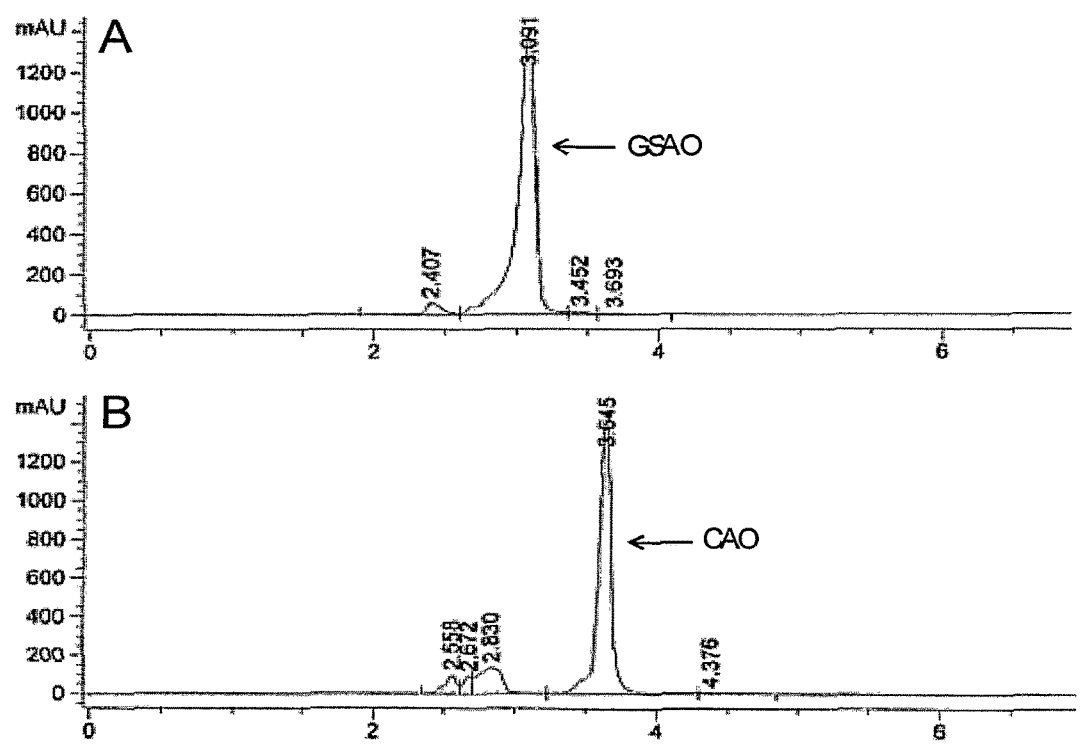
FIG. 15. HPLC analysis of GSAO and CAO. 5 nmoles of GSAO (part A) or CAO (part B) was resolved on a C18 reverse phase column and detected by absorbance at 256 nm.

GSAO and CAO were characterized by HPLC (1200 Series; Agilent Technologies, Santa Clara, Calif.). Samples were resolved on a Zorbax Eclipse XDB-C18 column (4.6× 150 mm, 5 µm; Agilent Technologies) using a mobile phase of acetonitrile-water (25:75 vol/vol), flow rate of 0.5 ml·min$^{-1}$ and detection by absorbance at 256 nm (FIG. 15).

Accumulation of GSAO and CAO in BAE Cells

Depending on the type of experiments, $1.6 \times 10^6$ or $7.5 \times 10^5$ BAE cells were seeded in petri dishes or 6-well-plates, respectively, and allowed to attach overnight. The medium was replaced and the cells were incubated for 30 min in the absence or presence of acivicin or 4H10. The cells were then incubated with 50 or 100 µM GSAO or CAO for 30 mM for 4 h. Cells were then washed twice with ice-cold PBS and lysed with 1 ml of 70% w/w nitric acid. Lysates were diluted 30-fold and analyzed for arsenic atoms using an Elan 6100 Inductively Coupled Plasma Spectrometer (Perkin Elmer Sciex Instruments, Shelton, Conn.).

Mitochondrial Swelling Assay.

Mitochondria were isolated from the livers of ~20 g female BalbC nude mice using differential centrifugation as described previously (Dilda et al., 2005a). The final mitochondrial pellet was resuspended in 3 mM Hepes-KOH, pH 7.0 buffer containing 213 mM mannitol, 71 mM sucrose and 10 mM sodium succinate at a concentration of 30 mg of protein per mL. Mitochondrial permeability transition induction was assessed spectrophotometrically by suspending the liver mitochondria at 1 mg of protein per ml at 37° C. in 3 mM Hepes-KOH, pH 7.0 buffer containing 75 mM mannitol, 250 mM sucrose, 10 mM sodium succinate, and 2 mM rotenone (Dilda et al., 2005a). Swelling was measured by monitoring the associated decrease in light scattering at 520 nm using a Molecular Devices M2 Microplate Reader (Palo Alto, Calif.).

Results and Discussion

CAO Accumulates More Rapidly in Cells and Have Greater Anti-Proliferative Activity than GSAO.

4-(N—(S-cysteinylacetyl)amino)phenylarsinous acid (CAO) was produced by enzymatic cleavage of GSAO and its accumulation in endothelial cells and effects on cell proliferation was measured. 4-(N—(S-cysteinylglycylacetyl)amino)-phenylarsinous acid was produced by cleaving the γ-glutamyl group from GSAO with ovine kidney γ-glutamyl transpeptidase, and 4-(N—(S-cysteinylacetyl)amino)-phenylarsinous acid (CAO) was produced by cleaving the glycine amino acid from this intermediate with porcine kidney aminopeptidase N (FIG. 14). The enzymes were removed from the reactions by size-exclusion filtration.

Figure 16:
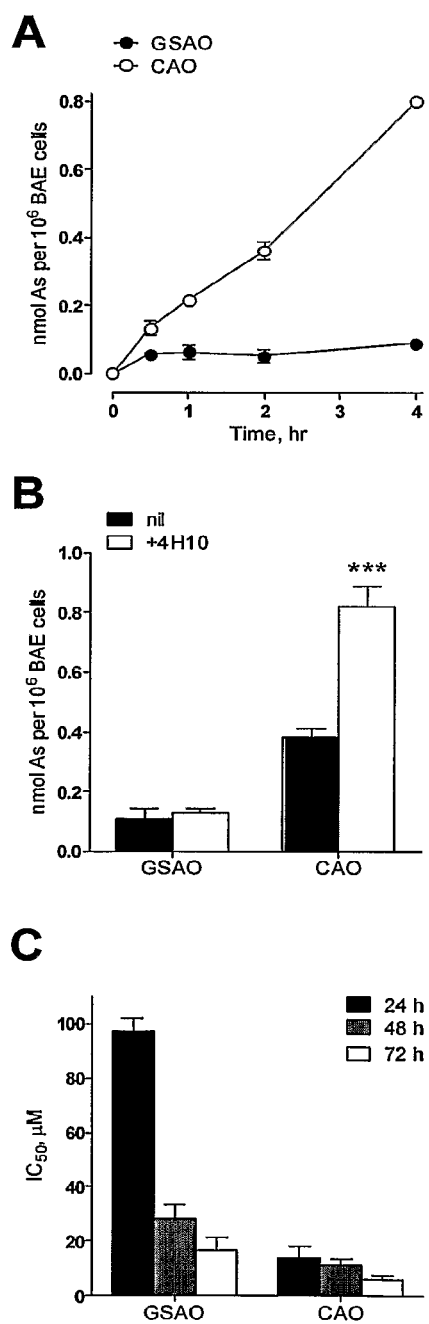
FIG. 16. CAO accumulates more rapidly in cells and have greater anti-proliferative activity than GSAO. A. CAO accumulates in cells at a much faster rate than GSAO. BAE cells were incubated with 50 μM GSAO or CAO for 4 h. Cellular arsenic levels were determined by ICPMS. The rates of accumulation are GSAO and CAO are 0.03 and 0.20 nmol As atoms per $10^6$ cells, respectively. Data points are the mean±SD of three determinations. The results are representative of two experiments. B. CAO is exported from cells by the multidrug resistance associated protein 1. BAE cells pretreated for 30 min with 10 μM of the MRP-1 inhibitor 4H10 were incubated with 50 μM GSAO or CAO for 2 h. Cellular arsenic levels were determined by ICPMS. Data points are the mean±SD of three determinations. The results are representative of two experiments. C. GSAO and CAO $IC_{50}$ values for proliferation arrest of endothelial cells. BAE cells were incubated with 0.8-100 μM GSAO or CAO for 24, 48 or 72 h. Cell viability was determined using MTT. Results are expressed as percentage of control. Values are mean±SD of triplicate determinations. Results are representative of three experiments.

CAO accumulated in endothelial cells at a ~8-fold faster rate than GSAO (FIG. 16A). Cellular accumulation of these metabolites is a balance between rate of uptake and rate of export from the cell. GSAO accumulation in cells is controlled by rate of export by the multidrug resistance-associated proteins (MRP) 1 and 2 (Dilda et al., 2005b). To test whether CAO is also exported by MRP, the effect of the MRP-1 inhibitor, 4H10, on accumulation in endothelial cells was measured. Cellular accumulation of CAO was increased ~3-fold, respectively, when MRP-1 was inhibited (FIG. 16B). This finding implies that the increased accumulation of CAO in endothelial cells is predominantly due to increased rate of uptake.

The faster rate of accumulation of CAO in endothelial cells was anticipated to result in increased anti-proliferative activity. The $IC_{50}$'s for proliferation arrest of endothelial cells by GSAO and CAO in 24, 48 and 72 h assays is shown in FIG. 16C. It is clear from the results that the $IC_{50}$ for GSAO markedly decreases with time of incubation and much less so for CAO. For example, the 72 h GSAO $IC_{50}$ is similar to the 24 h $IC_{50}$ for CAO.

CAO Triggers the Mitochondrial Permeability Transition.

Figure 17:
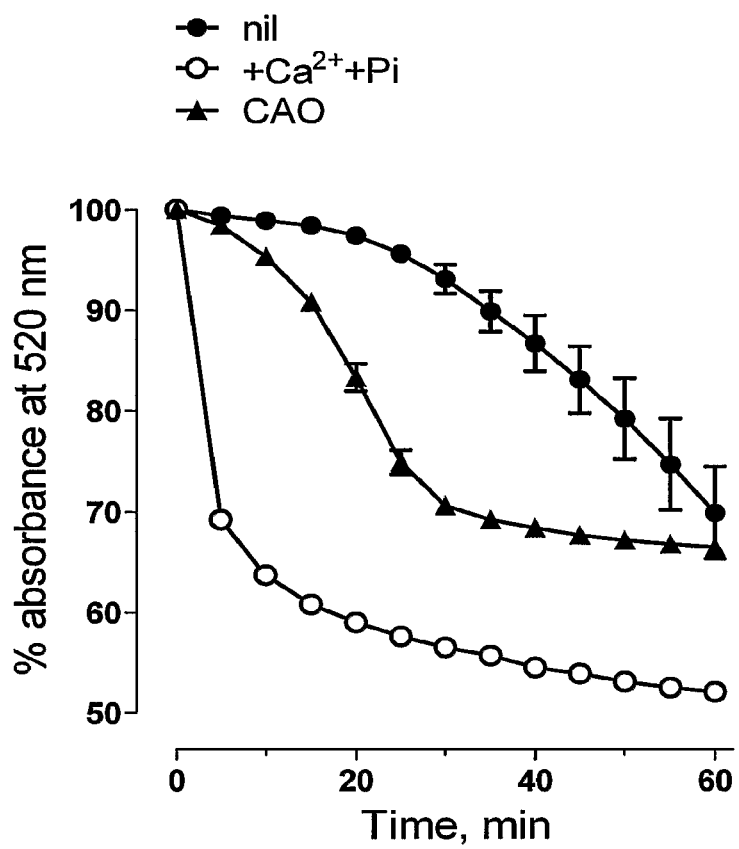
FIG. 17. CAO triggers the mitochondrial permeability transition. Mitochondria were incubated with nil (●), 150 μM $Ca^{2+}$ and 6 mM Pi (○) or 200 μM CAO (▲) and swelling monitored by decrease in light scattering at 520 nm over 60 min. The traces are representative of two experiments.

GSAO has been shown to inactivate the mitochondrial inner membrane transporter adenine nucleotide translocase (ANT), which leads to proliferation arrest and cell death (Don et al., 2003). CAO also induces the mitochondrial permeability transition (FIG. 17).

REFERENCES

Allen, J. D., Brinkhuis, R. F., Wijnholds, J., and Schinkel, A. H. (1999). The mouse Bcrp1/Mxr/Abcp gene: amplification and overexpression in cell lines selected for resistance to topotecan, mitoxantrone, or doxorubicin. Cancer Res 59, 4237-4241.

Dilda, P. J., Decollogne, S., Rossiter-Thornton, M., and Hogg, P. J. (2005a). Para to ortho repositioning of the arsenical moiety of the angiogenesis inhibitor 4-(N—(S-glutathionylacetyl)amino)phenylarsenoxide results in a markedly increased cellular accumulation and antiproliferative activity. Cancer Res 65, 11729-11734.

Dilda, P. J., Don, A. S., Tanabe, K. M., Higgins, V. J., Allen, J. D., Dawes, I. W., and Hogg, P. J. (2005b). Mechanism of selectivity of an angiogenesis inhibitor from screening a genome-wide set of Saccharomyces cerevisiae deletion strains. J Natl Cancer Inst 97, 1539-1547.

Don, A. S., Kisker, O., Dilda, P., Donoghue, N., Zhao, X., Decollogne, S., Creighton, B., Flynn, E., Folkman, J., and Hogg, P. J. (2003). A peptide trivalent arsenical inhibits tumor angiogenesis by perturbing mitochondrial function in angiogenic endothelial cells. Cancer Cell 3, 497-509.

Evens, A. M., Tallman, M. S., and Gartenhaus, R. B. (2004). The potential of arsenic trioxide in the treatment of malignant disease: past, present, and future. Leuk Res 28, 891-900.

Evers, R., Kool, M., Smith, A. J., van Deemter, L., de Haas, M., and Borst, P. (2000). Inhibitory effect of the reversal agents V-104, GF120918 and Pluronic L61 on MDR1 Pgp-, MRP1- and MRP2-mediated transport. Br J Cancer 83, 366-374.

Kobayashi, D., Nozawa, T., Imai, K., Nezu, J., Tsuji, A., and Tamai, I. (2003). Involvement of human organic anion transporting polypeptide OATP-B (SLC21A9) in pH-dependent transport across intestinal apical membrane. J Pharmacol Exp Ther 306, 703-708.

Kool, M., van der Linden, M., de Haas, M., Scheffer, G. L., de Vree, J. M., Smith, A. J., Jansen, G., Peters, G. J., Ponne, N., Scheper, R. J., et al. (1999). MRP3, an organic anion transporter able to transport anti-cancer drugs. Proc Natl Acad Sci USA 96, 6914-6919.

Reiter, A., Lengfelder, E., and Grimwade, D. (2004). Pathogenesis, diagnosis and monitoring of residual disease in acute promyelocytic leukaemia. Acta Haematol 112, 55-67.

Vey, N. (2004). Arsenic trioxide for the treatment of myelodysplastic syndromes. Expert Opin Pharmacother 5, 613-621.

Wolff, N. C., Randle, D. E., Egorin, M. J., Minna, J. D., and Ilaria, R. L., Jr. (2004). Imatinib mesylate efficiently achieves therapeutic intratumor concentrations in vivo but has limited activity in a xenograft model of small cell lung cancer. Clin Cancer Res 10, 3528-3534.

The invention claimed is:

1. A method of treating pancreatic cancer in a vertebrate, the method comprising administering to the vertebrate a therapeutically effective amount of a compound of general formula (I):

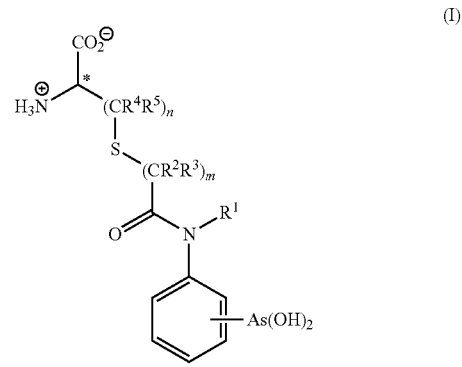

or a salt, enantiomer, or racemate thereof, wherein
the $As(OH)_2$ group is para- to the N-atom on the phenyl ring;
$R^1$ is selected from hydrogen and $C_{1-3}$ alkyl;
$R^2$ and $R^3$ are the same or different and are independently selected from hydrogen and optionally substituted $C_{1-3}$ alkyl;
$R^4$ and $R^5$ are the same or different and are independently selected from hydrogen and optionally substituted $C_{1-3}$ alkyl;

m is 1;
n is 1;
* indicates a chiral carbon atom; and
wherein each optional substituent is independently $C_{1-3}$ alkyl, $C_{1-3}$ alkoxy, halo, hydroxyl, or hydroxy($C_{1-3}$) alkyl.

2. The method according to claim 1, wherein $R^1$ is selected from hydrogen, methyl and ethyl.

3. The method according to claim 1, wherein $R^1$ is hydrogen.

4. The method according to claim 1, wherein $R^2$ and $R^3$ are independently selected from hydrogen, $C_{1-3}$ alkyl, hydroxy($C_{1-3}$)alkyl and halo($C_{1-3}$)alkyl.

5. The method according to claim 1, wherein $R^2$ and $R^3$ are independently selected from hydrogen, methyl, ethyl, hydroxymethyl, and $CF_3$.

6. The method according to claim 1, wherein $R^2$ and $R^3$ are independently selected from hydrogen, methyl and ethyl.

7. The method according to claim 1, wherein $R^2$ and $R^3$ are both hydrogen.

8. The method according to claim 1, wherein $R^4$ and $R^5$ are independently selected from hydrogen, $C_{1-3}$ alkyl, hydroxy-($C_{1-3}$)alkyl and halo($C_{1-3}$)alkyl.

9. The method according to claim 1, wherein $R^4$ and $R^5$ are independently selected from hydrogen, methyl, ethyl, hydroxy($C_{1-3}$)alkyl, and $CF_3$.

10. The method according to claim 1, wherein $R^4$ and $R^5$ are independently selected from hydrogen, methyl, ethyl and hydroxymethyl.

11. The method according to claim 1, wherein $R^4$ and $R^5$ are both methyl.

12. The method according to claim 1, wherein the $As(OH)_2$ group is para- to the N-atom on the phenyl ring; $R^1$ is hydrogen or methyl; $R^2$ and $R^3$ are independently selected from hydrogen, $C_{1-3}$ alkyl, hydroxy($C_{1-3}$)alkyl and halo($C_{1-3}$)alkyl; $R^4$ and $R^5$ are independently selected from hydrogen, $C_{1-3}$ alkyl, hydroxy($C_{1-3}$)alkyl and halo($C_{1-3}$) alkyl; m is 1; and n is 1.

13. The method according to claim 1, wherein the $As(OH)_2$ group is para- to the N-atom on the phenyl ring; $R^1$ is hydrogen or methyl; $R^2$ and $R^3$ are independently selected from hydrogen, methyl, ethyl, $CH_2OH$, and $CF_3$; $R^4$ and $R^5$ are independently selected from hydrogen, methyl, ethyl, $CH_2OH$, and $CF_3$ and $OCF_3$; m is 1; and n is 1.

14. The method according to claim 1, wherein the $As(OH)_2$ group is para- to the N-atom on the phenyl ring; $R^1$ is hydrogen or methyl; $R^2$ and $R^3$ are independently selected from hydrogen, methyl and ethyl; $R^4$ and $R^5$ are independently selected from hydrogen, methyl and ethyl; m is 1; and n is 1.

15. The method according to claim 1, wherein the $As(OH)_2$ group is para- to the N-atom on the phenyl ring; $R^1$ is hydrogen or methyl; $R^2$ is hydrogen or methyl; $R^3$ is hydrogen or methyl; $R^4$ is hydrogen, methyl or ethyl; $R^5$ is hydrogen or methyl; m is 1; and n is 1.

16. The method according to claim 1, wherein the $As(OH)_2$ group is para- to the N-atom on the phenyl ring; $R^1$ is hydrogen; $R^2$ is hydrogen or methyl; $R^3$ is hydrogen; $R^4$ hydrogen or methyl; $R^5$ is hydrogen or methyl; m is 1; and n is 1.

17. The method according to claim 1 wherein the compound of general formula (I) has the following structural formula:

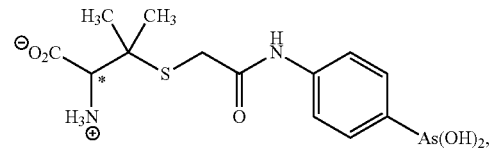

or a salt, enantiomer or racemate thereof.

18. The method according to claim 17, wherein the stereochemistry at the chiral carbon denoted * is (S), or a salt thereof.

19. The method according to claim 1 wherein the compound inhibits angiogenesis in the vertebrate.

20. The method according to claim 1 wherein the compound selectively induces the MPT in proliferating cells in the vertebrate.

21. The method according to claim 1 wherein the compound induces apoptosis of the proliferating cells.

22. The method according to claim 1, wherein the cells are endothelial cells.

* * * * *